US012672813B2

(12) United States Patent
Kruger et al.

(10) Patent No.: US 12,672,813 B2
(45) Date of Patent: Jul. 7, 2026

(54) ARRHYTHMIA CLASSIFICATION USING MEASUREMENT OF CARDIAC ACTIVITY AND POWER ANALYSIS

(71) Applicant: THE REGENTS OF THE UNIVERSITY OF MICHIGAN, Ann Arbor, MI (US)

(72) Inventors: Grant Kruger, Ann Arbor, MI (US); Hakan Oral, Ann Arbor, MI (US); Omer Berenfeld, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 446 days.

(21) Appl. No.: 18/034,774

(22) PCT Filed: Oct. 29, 2021

(86) PCT No.: PCT/US2021/057315
§ 371 (c)(1),
(2) Date: May 1, 2023

(87) PCT Pub. No.: WO2022/094252
PCT Pub. Date: May 5, 2022

(65) Prior Publication Data
US 2023/0414154 A1 Dec. 28, 2023
Related U.S. Application Data

(60) Provisional application No. 63/107,194, filed on Oct. 29, 2020.

(51) Int. Cl.
*A61B 5/361* (2021.01)
*A61B 5/00* (2006.01)

(52) U.S. Cl.
CPC ............ *A61B 5/361* (2021.01); *A61B 5/6861* (2013.01); *A61B 5/6882* (2013.01);
(Continued)

(58) Field of Classification Search
None
See application file for complete search history.

(56) References Cited

U.S. PATENT DOCUMENTS 5,833,603 A * 11/1998 Kovacs ..................... G01J 3/02
600/109
7,468,055 B2 12/2008 Prais et al.
(Continued)

FOREIGN PATENT DOCUMENTS

WO WO-2020224896 A1 * 11/2020 ......... A61N 1/36842

OTHER PUBLICATIONS

Chen et al., An Injectable 64 nW ECG Mixed-Signal SoC in 65 nm for Arrhythmia Monitoring, IEEE Journal of Solid-State Circuits, vol. 50, No. 1, Jan. 2015 (Year: 2015).*
(Continued)

*Primary Examiner* — Carl H Layno
*Assistant Examiner* — Manolis Pahakis
(74) *Attorney, Agent, or Firm* — MARSHALL, GERSTEIN & BORUN LLP; William J. Samore

(57) ABSTRACT

The following relates generally to an injectable cardiac monitor. In some embodiments, an injectable cardiac monitor includes: a sensor configured to detect a cardiac signal from a mammal, a processor configured to process the detected cardiac signal, a transmitter configured to transmit the processed signal to a computing device, and a capsule for injecting into the mammal. In some implementations, the capsule includes: a body configured to enclose all of the sensor, the processor, and the transmitter, and wings configured to, upon deployment into the mammal, deploy outwardly from the body of the capsule.

19 Claims, 18 Drawing Sheets

(52) U.S. Cl.
   CPC ................. *A61B 2560/0219* (2013.01); *A61B*
              *2560/0481* (2013.01); *A61B 2560/063*
                                         (2013.01)

(56)                 References Cited

U.S. PATENT DOCUMENTS

|  |  |  |  |
|---|---|---|---|
| 7,738,936 B1 * | 6/2010 | Turcott ................ | A61B 5/4035 |
|  |  |  | 600/339 |
| 8,905,910 B2 | 12/2014 | Reichenbach et al. |  |
| 9,037,223 B2 | 5/2015 | Oral et al. |  |
| 9,113,910 B2 | 8/2015 | Pachon Mateos et al. |  |
| 9,186,089 B2 | 11/2015 | Mazar et al. |  |
| 9,320,440 B2 | 4/2016 | Kyal et al. |  |
| 9,955,887 B2 | 5/2018 | Hughes et al. |  |
| 10,314,498 B2 | 6/2019 | Van Bladel et al. |  |
| 10,542,961 B2 | 1/2020 | Barsimantov et al. |  |
| 11,400,299 B1 * | 8/2022 | Gross ................... | A61N 1/3756 |
| 2004/0230279 A1 * | 11/2004 | Cates ................ | A61N 1/36585 |
|  |  |  | 607/126 |
| 2005/0015014 A1 | 1/2005 | Fonseca et al. |  |
| 2007/0156085 A1 * | 7/2007 | Schulhauser ........ | A61B 5/0084 |
|  |  |  | 604/66 |
| 2008/0300660 A1 * | 12/2008 | John ........................ | H04B 1/40 |
|  |  |  | 607/61 |
| 2011/0257491 A1 | 10/2011 | Robertson et al. |  |
| 2013/0192611 A1 * | 8/2013 | Taepke, II .......... | A61N 1/37518 |
|  |  |  | 128/898 |
| 2014/0155768 A1 | 6/2014 | Orion et al. |  |
| 2016/0338733 A1 | 11/2016 | Shah et al. |  |
| 2017/0127975 A1 * | 5/2017 | Bozkurt ............... | A01K 29/005 |
| 2018/0256905 A1 * | 9/2018 | Francia ................ | A61N 1/3956 |
| 2019/0021610 A1 | 1/2019 | Doan et al. |  |
| 2019/0029639 A1 | 1/2019 | Gifford, III et al. |  |
| 2019/0083801 A1 * | 3/2019 | Yang .................. | A61N 1/37518 |
| 2020/0023186 A1 * | 1/2020 | Reddy .................. | A61N 1/0563 |
| 2020/0029812 A1 * | 1/2020 | Govari .................... | A61B 5/25 |
| 2020/0029842 A1 | 1/2020 | Felix et al. |  |
| 2020/0038669 A1 * | 2/2020 | Manicka .............. | A61N 1/3956 |
| 2020/0077892 A1 | 3/2020 | Tran |  |
| 2020/0085312 A1 | 3/2020 | Tzvieli et al. |  |
| 2021/0000345 A1 * | 1/2021 | Felix ........................ | H04Q 9/00 |
| 2022/0077085 A1 * | 3/2022 | Henschel .......... | H01L 21/76898 |

OTHER PUBLICATIONS

International Search Report and Written Opinion for PCT Application No. PCT/US2021/057315 mailed Feb. 3, 2022.

* cited by examiner

Step 4: Stylet
Rotates Device
180° To Deploy
Stabilization
Wings.

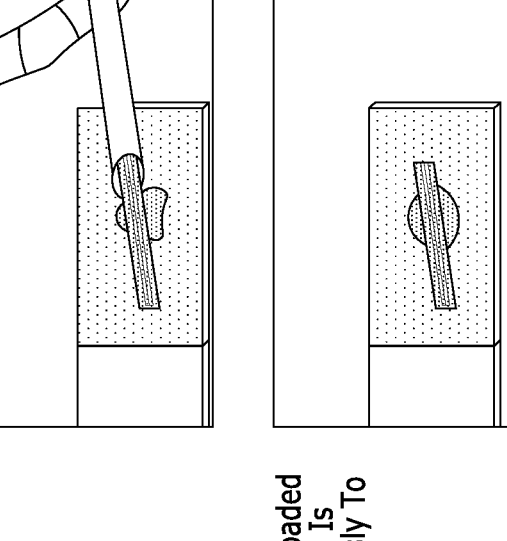

Step 5: Stylet
And Cannula
Are Removed

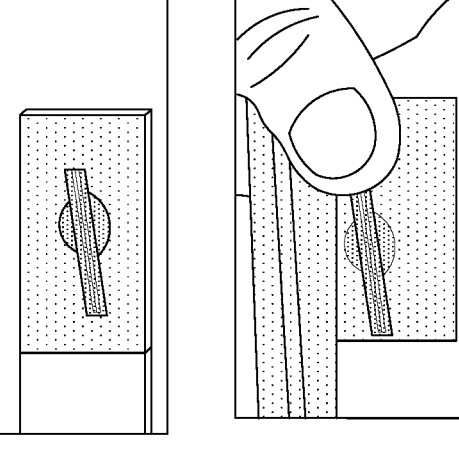

Step 6: Smartphone
Can Now Be Used To
Charge And Exchange
Data With The Device

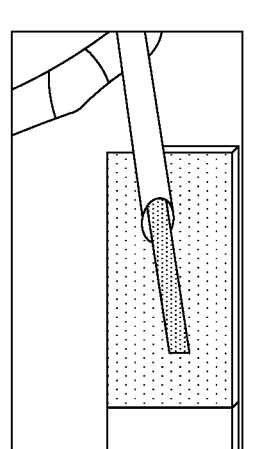

Step 1: A Small
Incision Is
Made In The
Skin.

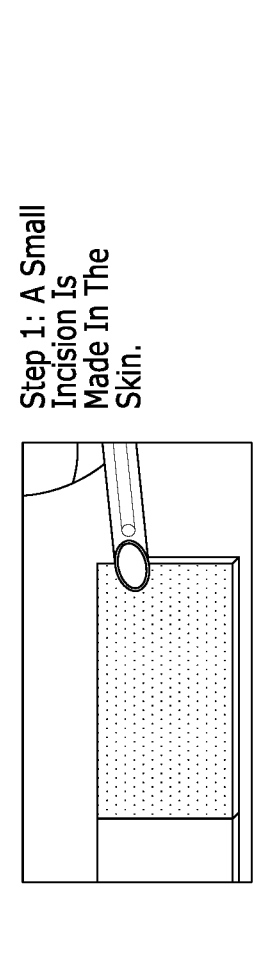

Step 2: Cannula Pre-Loaded
With Device And Stylet Is
Inserted Subcutaneously To
Create A Pocket.

Step 3: Cannula Is
Retracted While Stylet
Remains Stationary To
Deploy Device.

FIG. 4

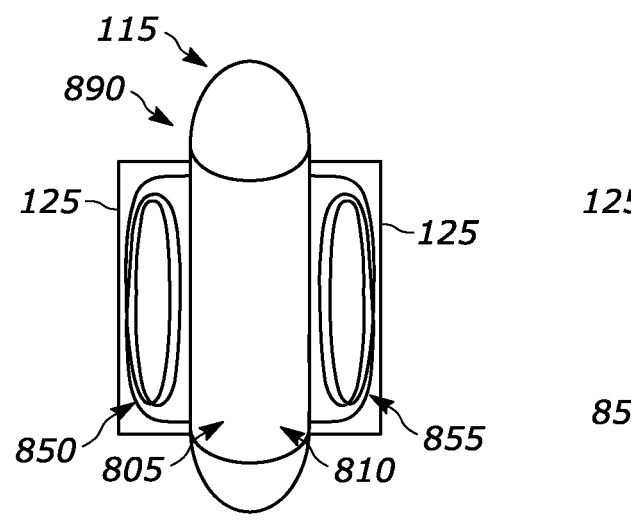
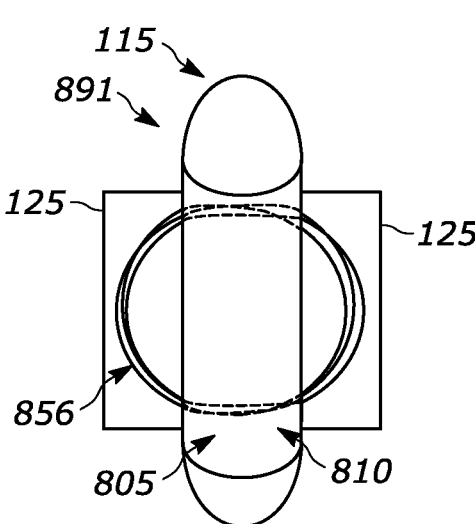
FIG. 8G
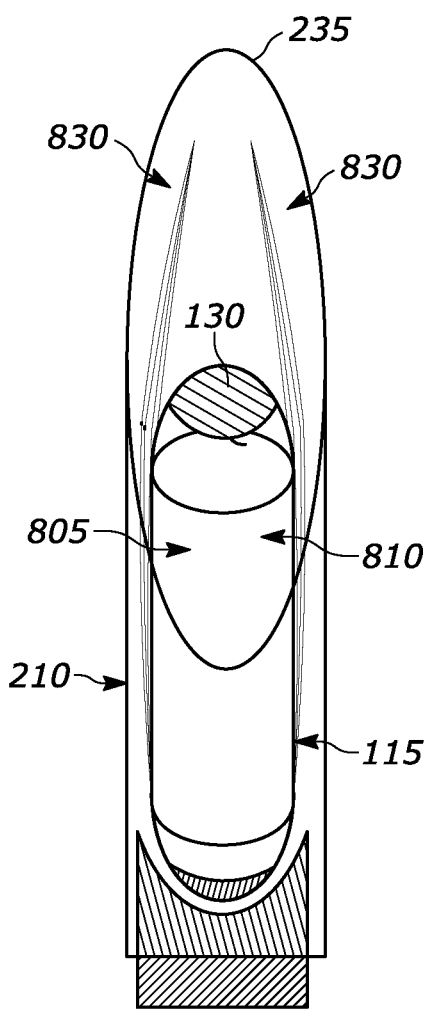
FIG. 8H
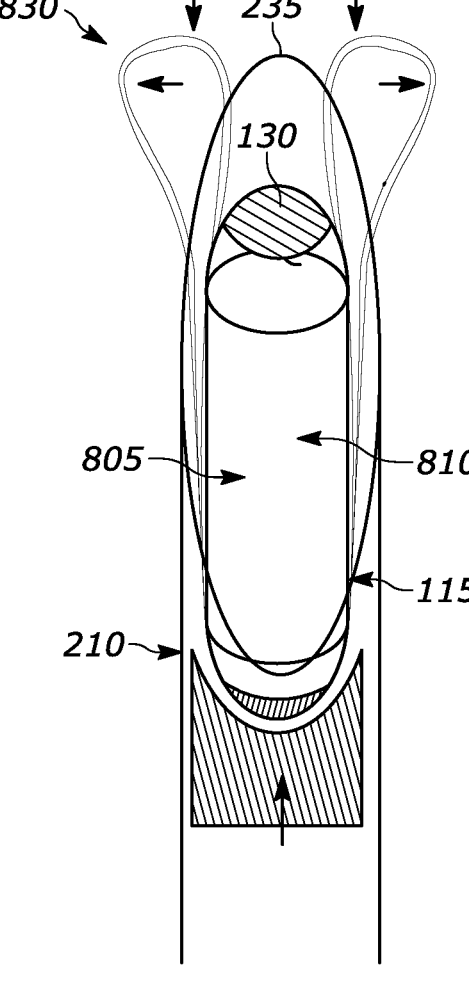
FIG. 8I

Protrusions For Continuous Track Between Casing And Needle

12°

19.50

23.80

Protrusions For Continuous Track Between Casing And Needle

17°

ARRHYTHMIA CLASSIFICATION USING MEASUREMENT OF CARDIAC ACTIVITY AND POWER ANALYSIS

CROSS REFERENCE TO RELATED APPLICATIONS

This application is a National Stage Application of PCT/US21/57315, entitled "Arrhythmia Classification Using Measurement Of Cardiac Activity And Power Analysis," filed Oct. 29, 2021, which claims the benefit of U.S. Provisional Patent Application No. 63/107,194, entitled "Arrhythmia Classification Using Measurement of Cardiac Activity and Power Analysis," Oct. 29, 2020.

BACKGROUND

Atrial Fibrillation (AF) is the most common cardiac arrhythmia, affecting over 33 million people worldwide, and presenting a significant independent risk factor for stroke and thromboembolism. In this regard, the electrocardiogram (ECG) is a common tool to assess cardiac function in health and disease. In recent years, many wearable ECG monitors have made their way to the market, but those generally provide only low positive predictive values and are not widely adopted by expert clinicians.

The systems and methods disclosed herein provide solutions to these problems and others.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one aspect, there is an injectable cardiac monitor device. The injectable cardiac monitor device may include: a sensor configured to detect a cardiac signal from a mammal; a processor configured to process the detected cardiac signal; a transmitter configured to transmit the processed signal to a computing device; energy storage and harvesting units and a capsule for injecting into the mammal. The capsule may include: a body configured to enclose all of the sensor, the processor, and the transmitter; and a wing configured to, upon deployment into the mammal, deploy outwardly from the body of the capsule.

In another aspect, there is an injectable cardiac monitor device. The injectable cardiac monitor device may include: a sensor configured to detect a cardiac signal from a mammal; a processor configured to process the detected cardiac signal; a transmitter configured to transmit the processed signal to a computing device; and a capsule. The capsule may be configured to enclose all of the sensor, the processor, and the transmitter. The capsule may further be configured to: prior to injection into the mammal, be in a rolled state so as to fit into an injector; and upon injection into the mammal, unroll into an unrolled state.

Advantageously, the techniques described herein provide early and asymptomatic AF detection, and improve AF management. Moreover, the described injectable device is significantly less invasive and traumatic for the patient and the injection procedure is even be able to be performed in a more relaxed clinical setting (e.g., a physician's office). Further advantages will be recognized by the following disclosure.

BRIEF DESCRIPTION OF THE DRAWINGS

FIG. 4 illustrates an example method for subcutaneous injection of the capsule using mock components in a phantom model of the skin.

FIG. 8G illustrates two example embodiments including coils in the wings.

FIGS. 8H-8J show an example process of injecting a capsule. Specifically, FIG. 8H shows an example of a capsule contained in the injector. FIG. 8I shows an example of the capsule partially injected out of the injector. FIG. 8J shows an example of the capsule separated from the injector.

FIG. 8K illustrates an example with a mat embedded in the wings.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

DETAILED DESCRIPTION

Overview

Figure 1:
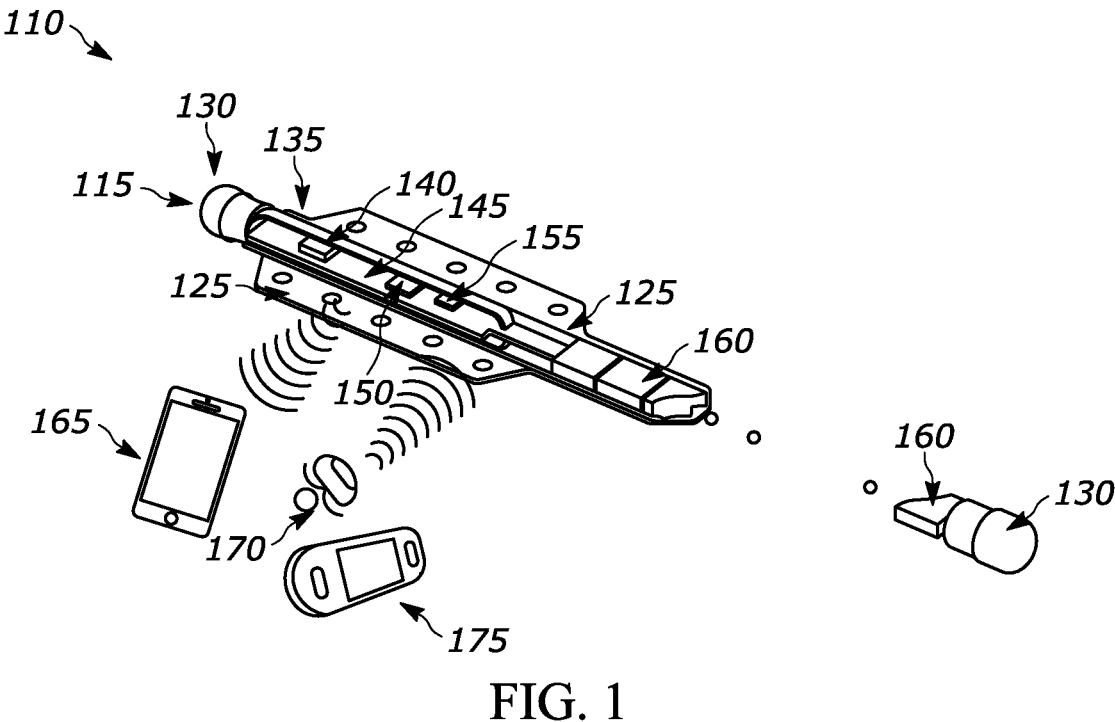
FIG. 1 illustrates an example injectable cardiac monitor.

The following relates generally to an injectable cardiac monitor device. In this regard, and by way of brief overview, FIG. 1 illustrates an example injectable cardiac monitor device 110. In the example of FIG. 1, the injectable cardiac monitor device 110 includes capsule 115 having wings 125 to stabilize the capsule 115. The illustrated capsule 115 also includes sensors 130 to receive the cardiac signal, and further comprises substrate 145 (e.g., a multi-layer polyamide printed circuit board (PCB) substrate).

Further illustrated are energy receiving components 135 for inductive energy harvesting; ECG front end 140 (e.g., a 68 nW single-lead ECG front end); processor 150; data storage 155 (e.g., non-volatile data storage); and energy storage 160 (e.g., a capacitor stage or electric double-layer capacitor (EDLC) system). The injectable cardiac monitor 110 may be in communication with a mobile device 165 (e.g., a smartphone, tablet, laptop, etc.), a patch device 170, and/or a handheld device 175 (e.g., a dedicated handled device dedicated to the injectable monitor device 110). The communication may be accomplished through a wireless communication link and protocol or through any suitable manner. For instance, the communication may be via a ISO 14443 compliant near field communication (NFC) interface for data transfer and charging. In some embodiments, the energy receiving components 135 are also transmitters (e.g., the energy receiving components 135 are coils). In some embodiments, the transmitter is a separate component from the energy receiving components 135.

Broadly speaking, any techniques may be used to detect AF or other cardiac condition. For instance, the techniques described in U.S. Pat. No. 9,037,223, may be used. U.S. Pat. No. 9,037,223 was filed Jan. 10, 2013, was granted May 19, 2015, is titled Atrial Fibrillation Classification Using Power Measurement, and is incorporated by reference in its entirety.

Injector Device—Brief Overview

Figure 2:
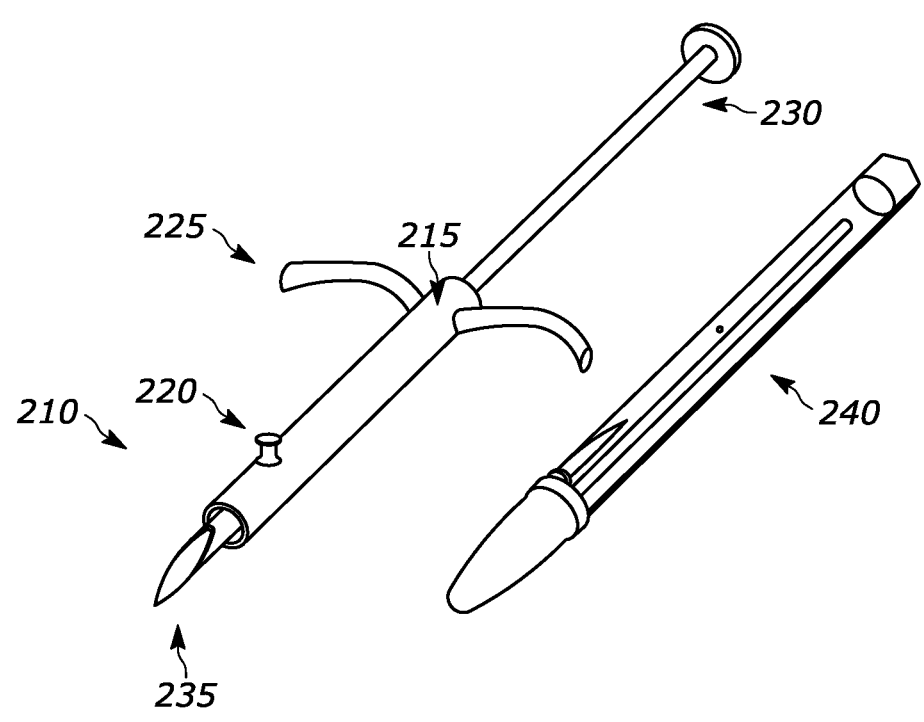
FIG. 2 illustrates an example injector for injecting an injectable cardiac monitor, such as the injectable cardiac monitor illustrated in FIG. 1.

To inject the injectable cardiac monitor 110, some embodiments use an injector. In this regard, FIG. 2 illustrates an example injector 210. With reference thereto, case 215 is configured to hold injectable cardiac monitor 110. Locking device 220 secures the injectable cardiac monitor 110. For example, when the locking device 220 is in a first position, the locking device 220 prevents release of the injectable cardiac monitor 110; and, when the locking device 220 is in a second position, the locking device 220 allows release of the injectable cardiac monitor 110.

Further, handles 225 and syringe push-rod 230 further facilitate the injection of the injectable cardiac monitor 110. Beveled and short needle 235 enables simple injection to a patient or mammal. FIG. 2 further shows a typical pen 240 for reference.

Moreover, the injector 210 provides a way to efficiently puncture the skin and orient the injectable cardiac monitor 110 correctly. Further, the needle 210 is designed as a dual bevel to allow for smooth insertion and minimal damage to the tissue.

As will be discussed in later sections of this disclosure, in-depth stress simulations and strain analyses were done to optimize the needle bevel angles, and analyze the forces that will be applied to the device to ensure that design requirements and specifications were met. The injector 210 may be pre-packaged and sterilized and designed for a onetime-use. Upon opening the package, the clinician may remove a cap of the needle 235, pinch a portion of the skin, insert the needle into the skin at a 90° angle at the place of insertion, and push on the plunger to insert the capsule under the skin.

Figure 3:
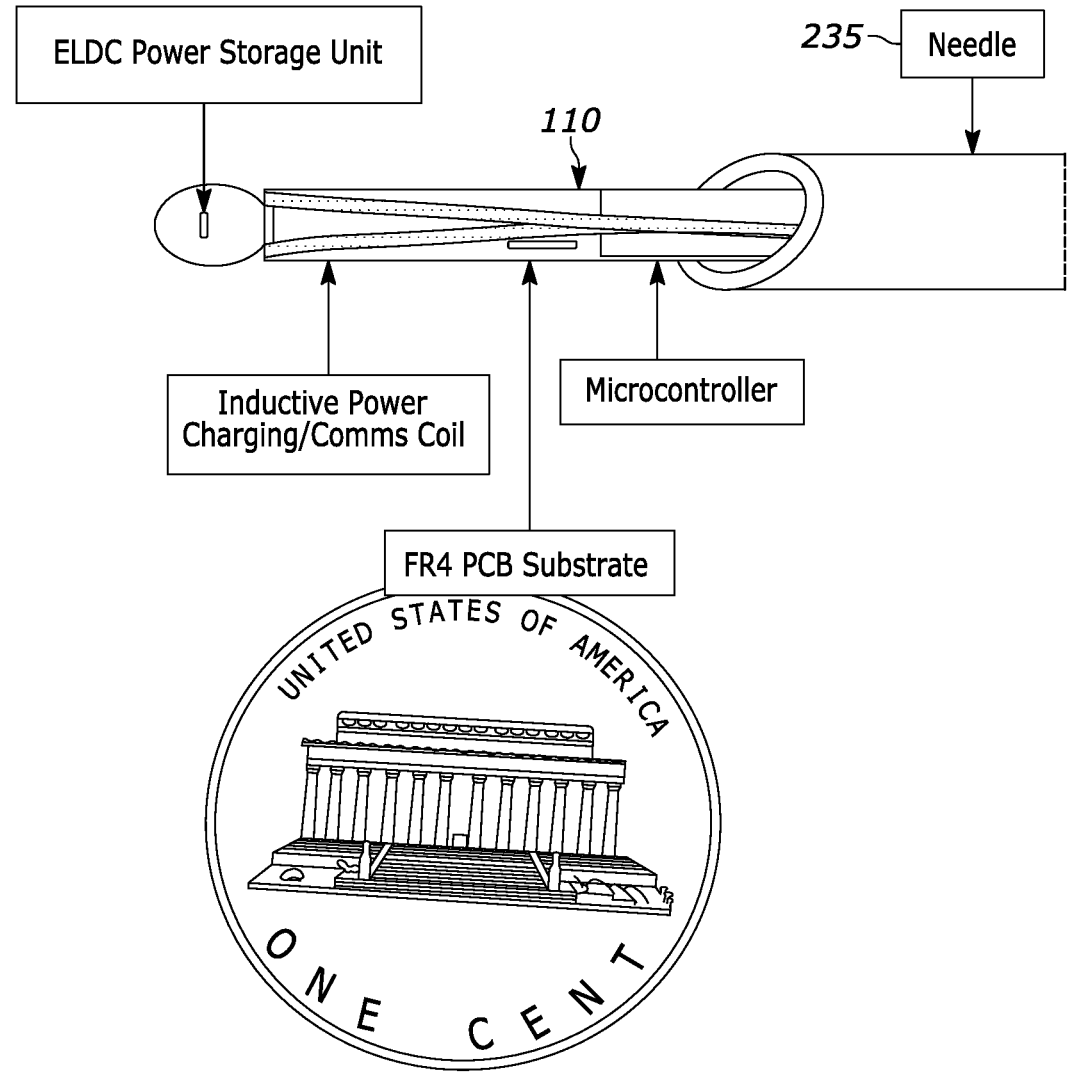
FIG. 3 illustrates an example of an injectable cardiac monitor protruding from a needle of an injector.

To further illustrate the interaction between the injectable cardiac monitor 110 and the injector 210, the example of FIG. 3 shows injectable cardiac monitor 110 protruding from needle 235 of an injector. The example of FIG. 3 further illustrates an ELDC power storage unit, a microcontroller, and a wireless power transfer/communications coil assembly.

FIG. 4 illustrates example steps for subcutaneous injection of the capsule using mock components in a phantom model of the skin. However, it should be noted that the example of FIG. 4 uses a different embodiment of the injector device than then example of FIG. 3. For instance, the example of FIG. 4 uses a cannula, and does not use a push rod.

In the example of FIG. 4, the following example steps are illustrated:

Step 1: A small incision of about 3 mm in diameter is cut in the patient skin, usually in the chest area.

Step 2: The cannula, which is pre-loaded with the injectable cardiac monitor 110 distally to a stylet, is inserted subcutaneously to create a pocket for the injectable cardiac monitor 110.

Step 3: The cannula is retracted while the stylet holding the injectable cardiac monitor 110 remains stationary.

Step 4: The stylet is rotated (e.g., by 180 degrees) to deploy a wing or wings of the injectable cardiac monitor 110, and release the injectable cardiac monitor 110 from the stylet. In this regard, in some embodiments, the cannula or injector has a non-round cross-section, thereby allowing the wing(s) to begin to deploy while the stylet is rotated and the injectable cardiac monitor is still partially in the cannula or injector.

Step 5: The stylet and the cannula are then pulled back leaving the injectable cardiac monitor 110 with its open wing(s) inside the subcutaneous pocket with a fixed orientation relative to the skin surface to optimize inductive energy harvesting and communication.

Step 6: An external device, such as the smartphone 165 of FIG. 1, equipped with a dedicated software app can be used to remotely and wirelessly charge and communicate with the device.

Interaction Between System Components

Figure 5:
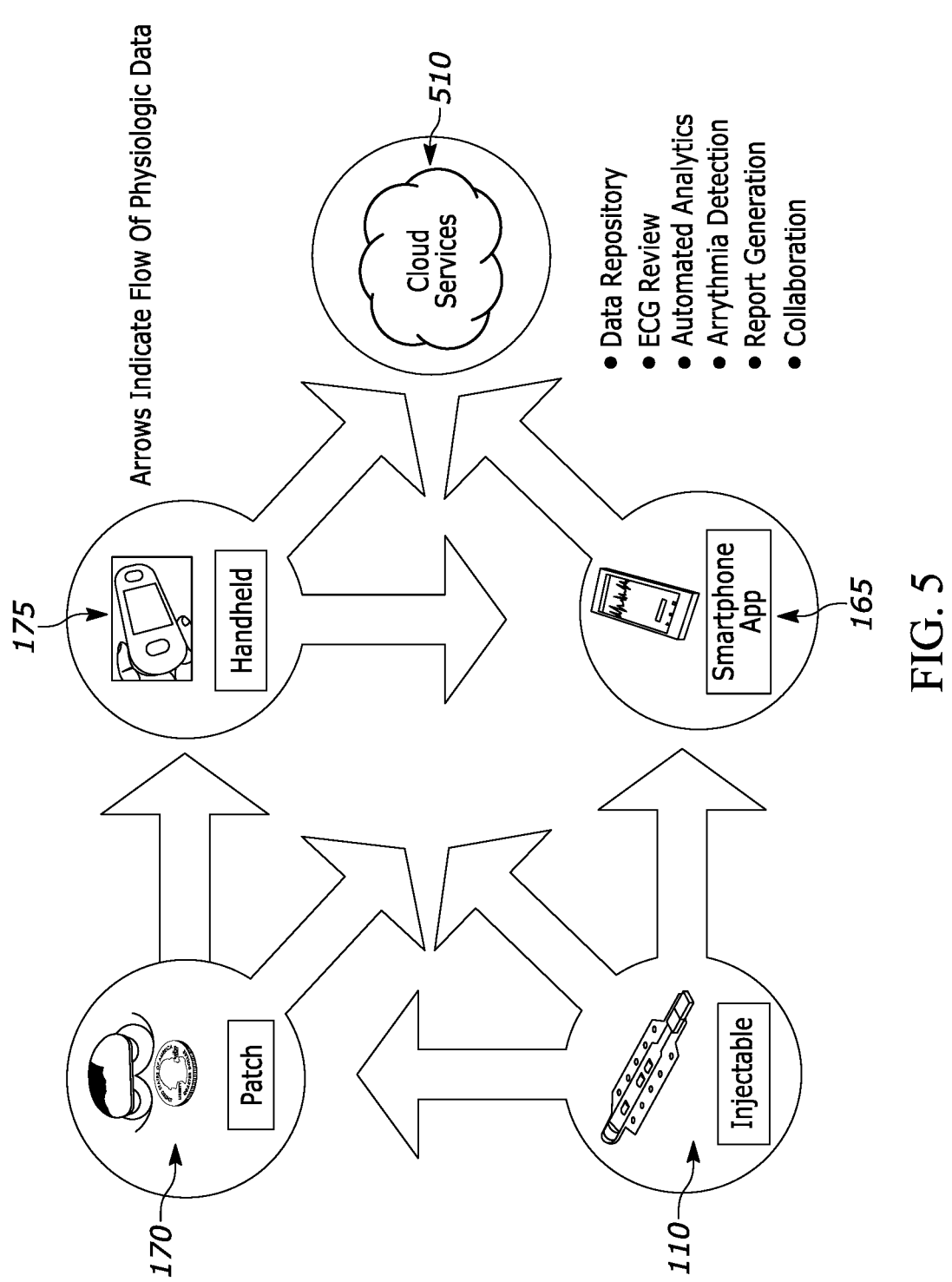
FIG. 5 illustrates example flows of data between system components.

Even though the described various devices can operate as stand-alone monitors, they also have the capability of being configured to support each other. In this regard, the example of FIG. 5 illustrates exemplary interactions between system components. In particular, the arrows indicate possible pathways via which physiologic data can flow from the patient to the cloud 510, where it is available for physician review. It should be noted that power, control codes and firmware updates could flow in the opposite direction of the arrows, but this was not indicated in FIG. 5 for clarity. For example, the injectable cardiac monitor 110 can be charged/powered and data transferred using either a smartphone 165, handheld device 175 or patch device 170. Hand-held device 175 would provide intermittent power transfer/data transfer (interrogation), whereas the patch 170 could provide continuous power transfer for long term monitoring and/or act as a data bridge to either collect and store large volumes of recorded data or stream the data via a Bluetooth/WiFi (or similar) link to a nearby smartphone 165, handheld device 175, bedside device, etc. From there, the data could be routed to a cloud server 510 for long term archiving, analysis, alerting and reporting.

Exemplary Handheld Device

Figure 6:
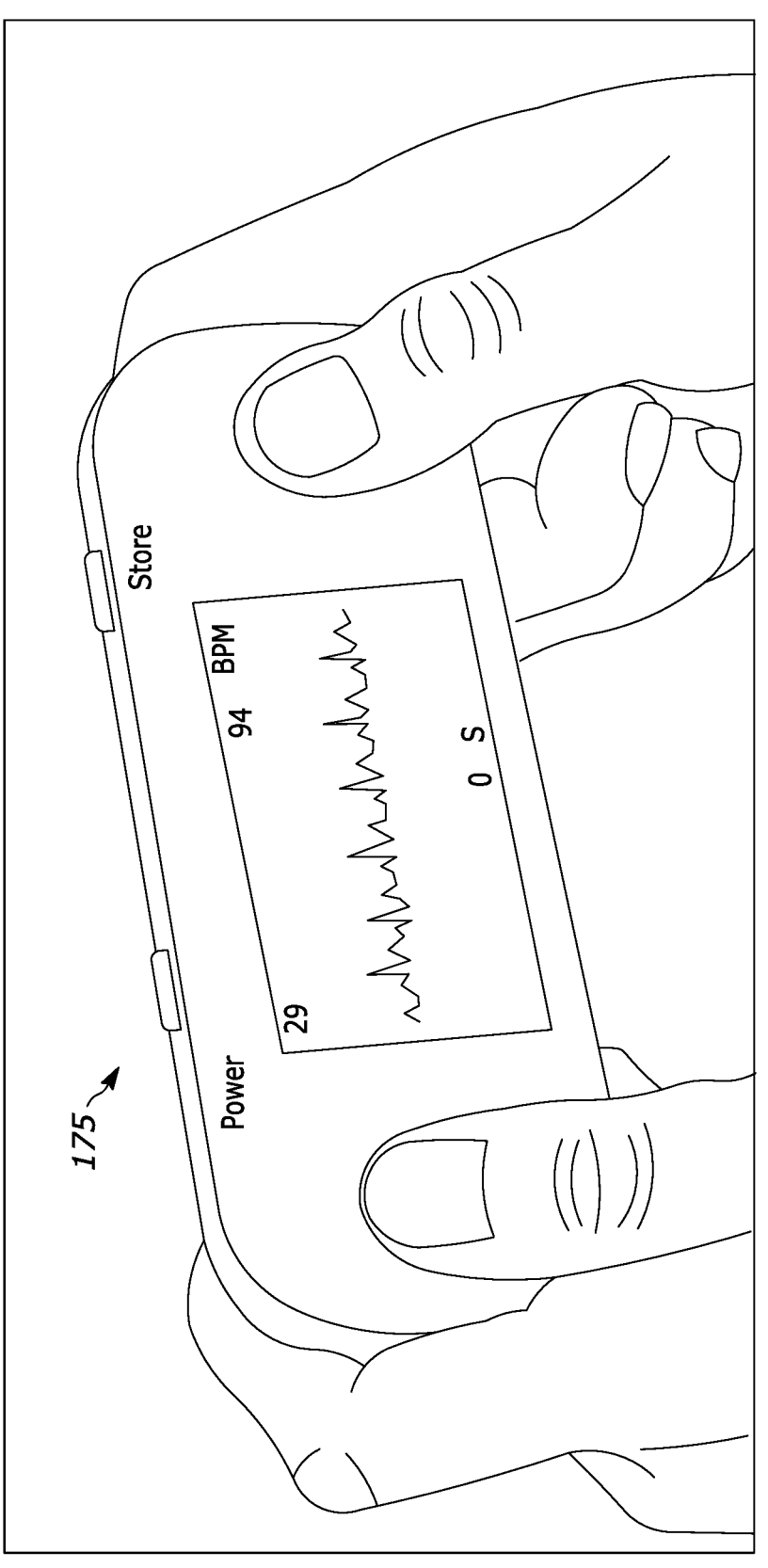
FIG. 6 illustrates an example handheld device.

FIG. 6 illustrates an example handheld device 175. In some embodiments, handheld device 175 has:

A compact, low-profile and ergonomic design.

Integrated dry electrodes for hand-held use.

An external adapter which provides up to 5-lead ECG recording capability using gel electrodes for ambulatory recording (e.g., Holter mode).

Long battery life for continuous recording time between charges. Also supported is additional external and/or high capacity internal battery for long-term Holter mode.

A full-color LCD display is provided with optional touch screen user interface.

Internal micro SD Card provides substantial non-volatile storage capacity.

Connectivity including USB, Bluetooth and/or WiFi.

Integrated AF detection algorithm.

Patch Device

Figure 7:
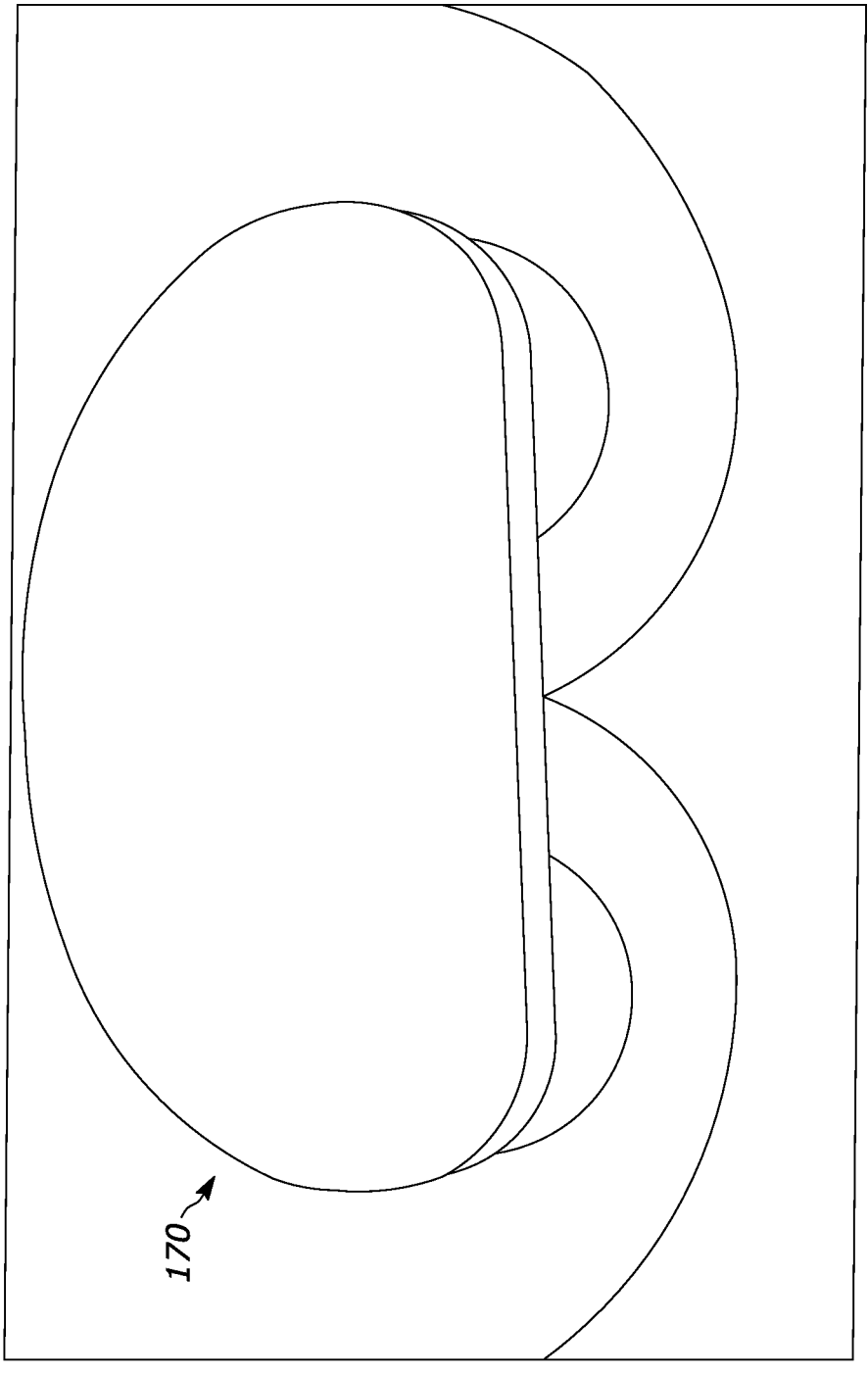
FIG. 7 illustrates an example patch device.

FIG. 7 illustrates an example patch 170. In some implementations, the patch 170 may be attached (e.g., by an adhesive or any other means) to a mammal, and may have electrodes that monitor a cardiac signal of the mammal. Thus, the patch 170 may be used as a replacement for, or as an addition to, the injectable cardiac monitor 110. In some embodiments, patch 170:

Is compact, ergonomic, low-profile and waterproof.

Includes an easily replaceable disposable gel electrode patch.

Has a 3-Lead ECG which improves motion artifact compensation.

Supports additional sensors: pulse oximetry, skin temperature, actigraphy, etc.

Is Bluetooth Low Energy (BLE) enabled.

Is capable of streaming data to smartphone (cloud) via Bluetooth for up to 2 weeks without battery replacement or charging.

Has optional rechargeable battery and wireless charging.

Is configurable as a data bridge for pairing with injectable cardiac monitor 110 for long-term data archiving and power transfer or for automatic sync/stream of implanted device data to a smartphone/cloud.

Mobile Device

In some implementations, the mobile device 165 may be in communication with the injectable cardiac monitor 110, and may also be used to wirelessly charge the injectable cardiac monitor 110. The mobile device 165 may include one or more processors and one or more memories.

The mobile device 165 may include a data transmitter for transmitting data to the injectable cardiac monitor 110, and further include a power transmitter for powering the injectable cardiac monitor 110. It should be noted that the data transmitter and power transmitter may be the same or different components. The mobile device 165 may further include a receiver for receiving data from the injectable cardiac monitor 110.

The mobile device 165 may further include a WiFi transmitter/receiver, a Bluetooth transmitter/receiver, and a cellular transmitter/receiver (e.g., for use on a 4G LTE network, a 5G network, etc.). In some embodiments, the WiFi transmitter/receiver, Bluetooth transmitter/receiver, or cellular transmitter/receiver acts as the data transmitter/receiver for communication with the mobile device 165. It should be understood that any of the aforementioned components may also be used to communicate with the patch 170 and/or handheld 175.

For user convenience, the mobile device 165 may run an app to control the injectable cardiac monitor 110. The app may further display information received from the injectable cardiac monitor 110 (e.g., on a touchscreen display of the injectable cardiac monitor 110).

Power

In some embodiments, the injectable cardiac monitor 110 is powered by a capacitor stage (e.g., the energy storage 160 comprises a capacitor stage). Using a capacitor stage rather than a battery is advantageous because a battery poses a toxicity risk and limited life-span.

Further advantageously, energy storage 160 is able to be wirelessly power leading to effective unlimited longevity of power. For example, energy receiving components 135 may inductively harvest energy from an external charging device (e.g., smartphone 165, patch 170, and so forth). For instance, the energy receiving components 135 may be coils, capacitive membranes, an array of photocells, thermal power receivers, electromagnetic power receivers, vibratory power receivers and/or an array of ultrasound receivers.

Furthermore, the injectable cardiac monitor 110 may send a ping requesting transmission of power. For example, the ping may be sent to any of the mobile device 165 (e.g., a smartphone, tablet, laptop, etc.), the patch device 170, and/or a handheld device 175 (e.g., a dedicated handled device dedicated to the injectable monitor device 110).

Due to the effective unlimited longevity of the proposed power source, periodic excision and reimplantation of a new device to continue monitoring may not be required. Finally, the ability of the device to be recharged and interrogated using the patient's smartphone significantly improves usability.

Any positioning of the energy receiving components 135 may be used. For example, the coil may run along a longitudinal axis of the body of the capsule 115. In some embodiments, there is a primary coil on a first wing of the capsule 115, and a secondary coil on a second wing of the capsule 115. FIG. 8G illustrates an example embodiment 890 with coils 850, 855 on the wings 125. FIG. 8G further illustrates example embodiment 891 with a single coil 856 that spans both of the wings 125. In this regard, by placing the coils 850, 855, 856 on the wings 125, some embodiments leverage the increased surface area of the wings 125 for increased efficiency in energy harvesting. The coils can be formed with the wings in various ways. The wings may be formed with integrated coil molded into layers of flexible biocompatible silicone forming the wings, in some examples. The wings may be formed with integrated coil and capsule thermoformed from biocompatible thermoplastic material, in other examples. The integrated coils 850, 855, 856 may be formed on a surface of the coil or embedded within the coil. As illustrated in FIG. 8G, in some examples, a single coil is used, which may span across wings, while in some examples, multiple coils may be used, with each wing have a coil. In some examples, the coils may be replaced with separate concentric coils, each electrically isolated and each configured for a different energy harvesting. Such a configuration would allow for separately controlling different coils based under different drive frequencies to charge different functioning aspects of the overall cardiac monitoring device.

Figure 8A:
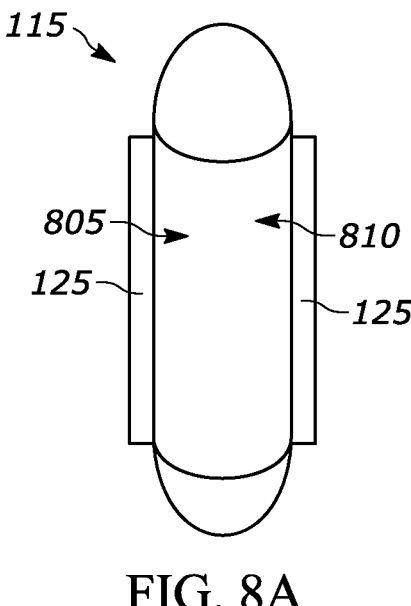
FIG. 8A illustrates an example of a top view of a capsule where the wings are attached to a first side and a second side of the capsule.
Figure 8B:
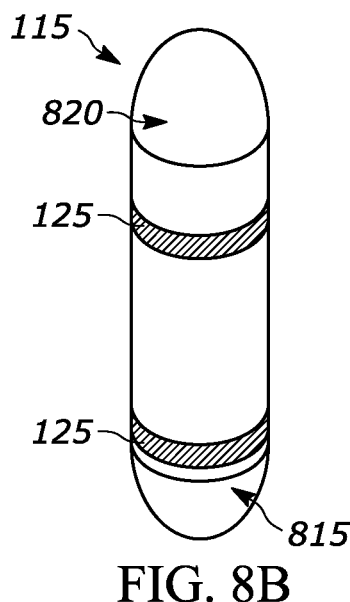
FIG. 8B illustrates a top view of a capsule where the wings are attached to a front end and a back end of the capsule.
Figure 8C:
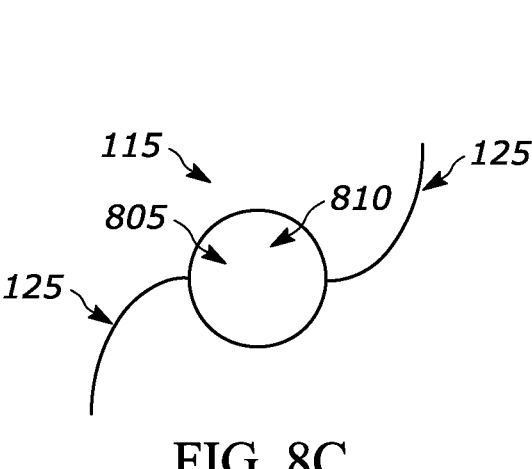
FIG. 8C illustrates a front view of a capsule where the wings unroll outwardly from the first side and/or the second side of the capsule.
Figure 8D:
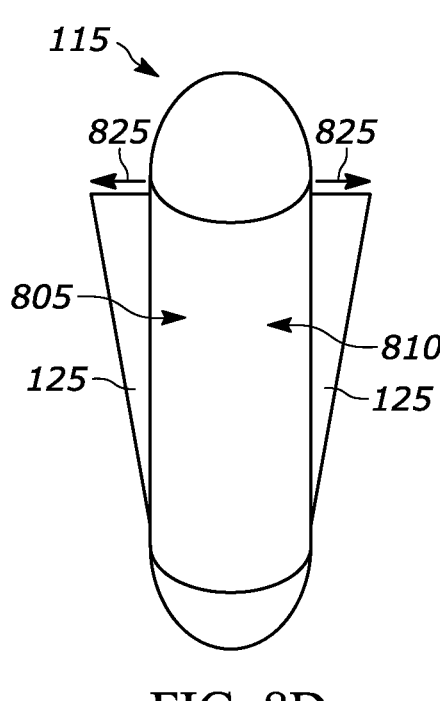
FIG. 8D illustrates a top view of a capsule where the wings expand in an umbrella-type motion from the first side and/or the second side of the capsule.
Figure 8E:
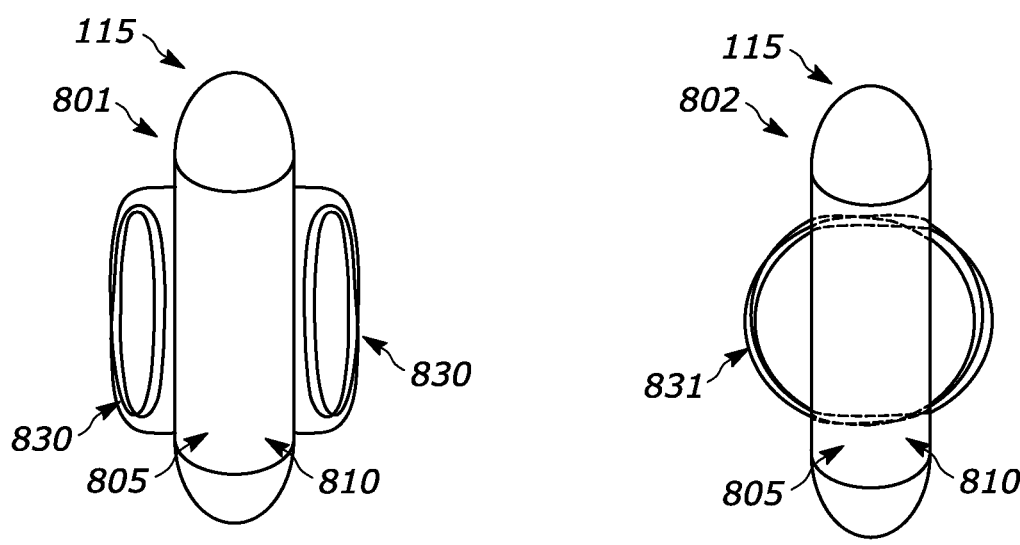
FIG. 8E illustrates two embodiments of a top view of a capsule where, for stabilization of the capsule, preformed coil(s) are deployed from the first side and/or the second side of the capsule.
Figure 8F:
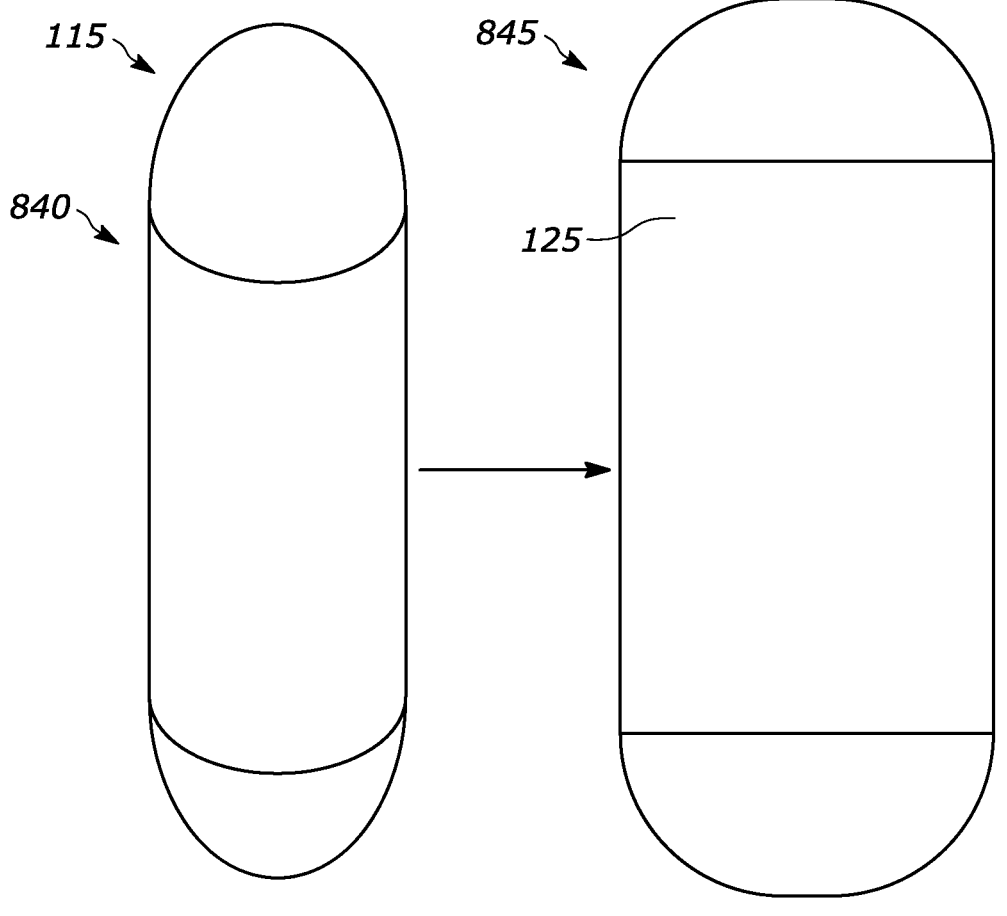
FIG. 8F illustrates a top view of an example of a capsule transitioning from a rolled state to an unrolled state.
Figures 8J, 8K:
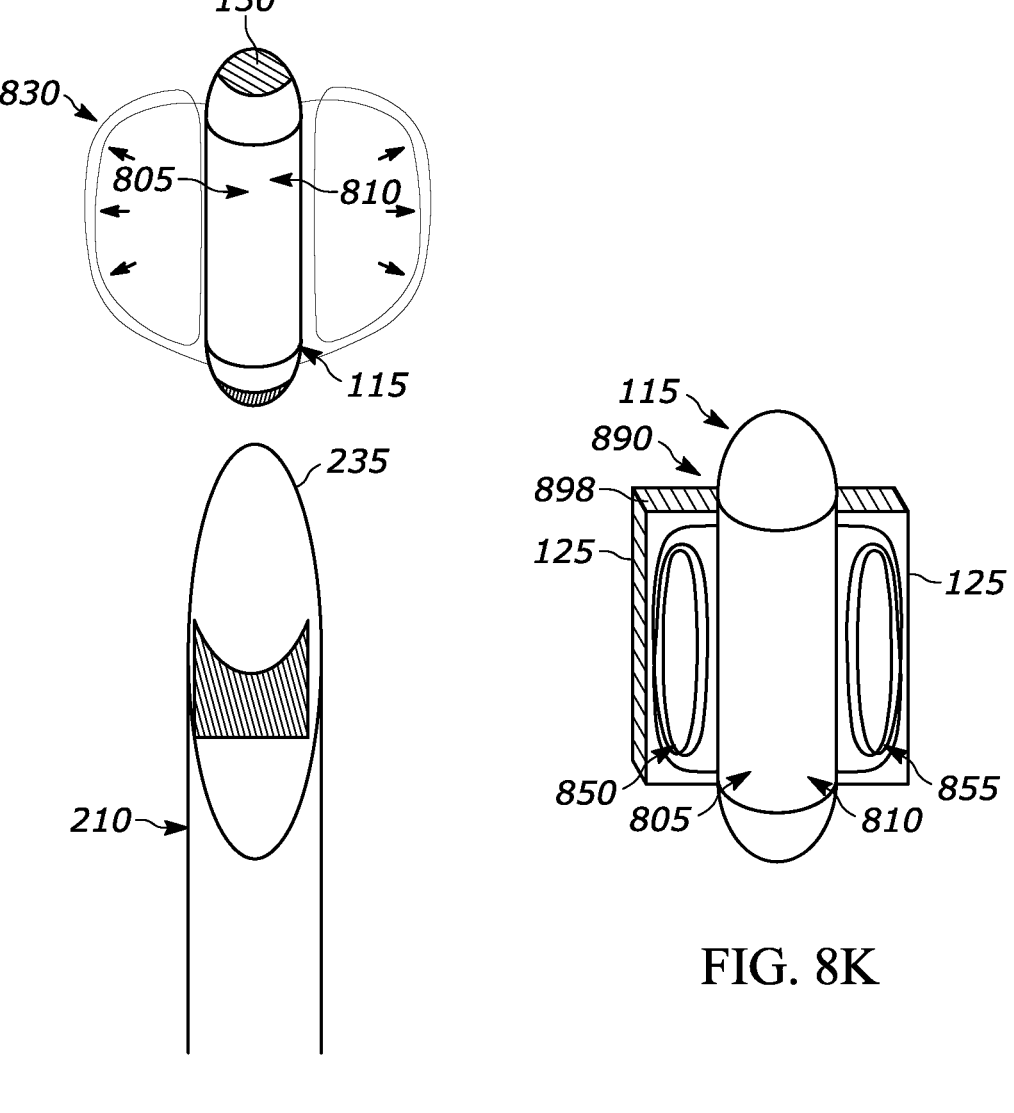

To further illustrate, FIGS. 8H-8J show an example process of injecting a capsule 115 without wings (e.g., in this example, the coils 830, rather than wings, provide stability). More specifically, FIG. 8H shows an example of a capsule 115 contained in the injector 210. In an exemplary next step, FIG. 8I shows an example of the capsule 115 partially injected out of the injector 210. Finally, FIG. 8J shows an example of the capsule 115 separated from the injector 210. As can be seen, in this example, the coils 830 expand as they are injected out of the injector 210.

FIG. 8K illustrates an example with a mat 898 embedded in the wings 125. In some embodiments, advantageously, the mat 898 is more permeable to magnetic fields than air, water, or tissue. For example, in some embodiments, the mat 898 may be made of ferromagnetic material formed by alloying Iron with Nickle and/or other materials. Thus, this mat 898 may advantageously help to increase the range of the wireless power transfer by providing a "short-cut" for the magnetic field (so it does not need to penetrate deep into the tissue beyond the coil layer).

Figures 8L, 8M:
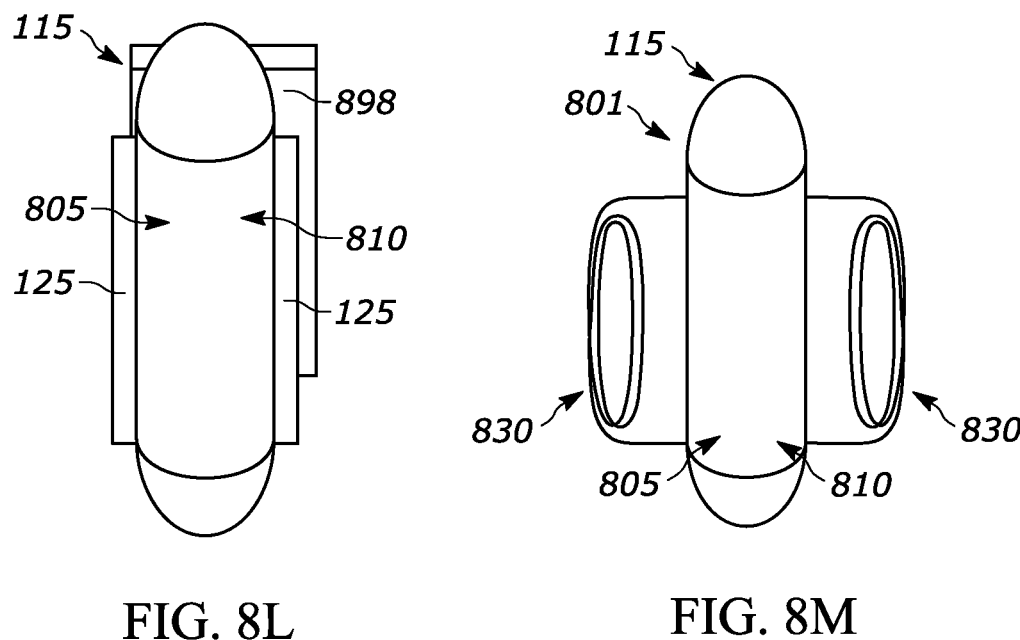
FIG. 8L illustrates an example of a mat detached from the capsule.
FIG. 8M illustrates an example where the coils are farther separated from the capsule than in the example of FIG. 8E, but still attached to the capsule by wires.

FIG. 8L illustrates an example of the mat (e.g., more permeable to magnetic fields than air, water, or tissue) 898 detached from the capsule. The mat 898 may be injected as part of the same injection or as part of a separate injection as the capsule 115. In some embodiments, the mat 898 comes preloaded into its own separate injector 210 for separate injection. The mat 898 may be positioned on any side of the capsule 115.

FIG. 8M illustrates an example where the coils 830 are farther separated from the capsule 115 than in the example of FIG. 8E, but still attached to the capsule 115 by wires.

Figures 8N, 8O:
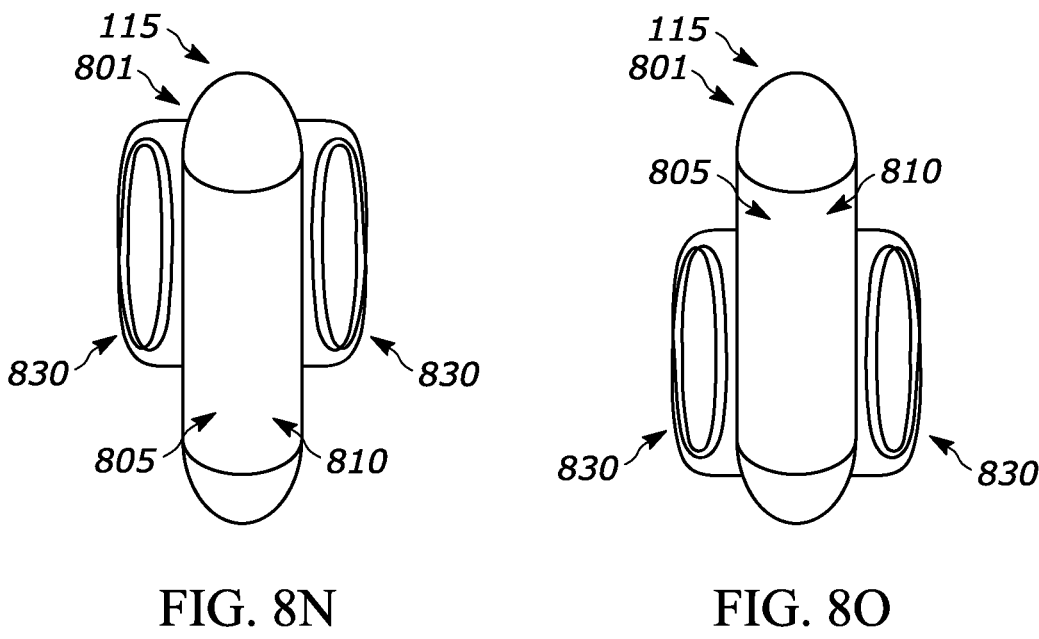
FIG. 8N illustrates an example where the coils are closer to a top of the capsule than in the example of FIG. 8E.
FIG. 8O illustrates an example where the coils are closer to a bottom of the capsule than in the example of FIG. 8E.

FIG. 8N illustrates an example where the coils 830 are closer to a top of the capsule 115 than in the example of FIG. 8E.

FIG. 8O illustrates an example where the coils 830 are closer to a bottom of the capsule 115 than in the example of FIG. 8E.

Figure 8P:
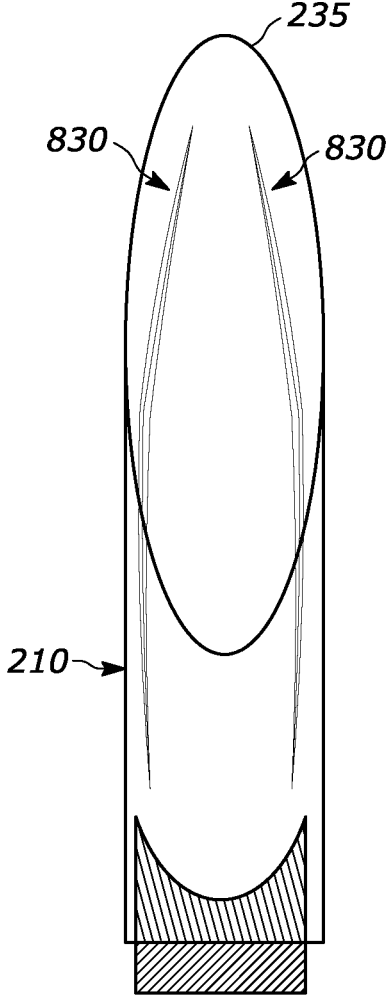
FIG. 8P illustrates an example of injecting a coil without a capsule.

FIG. 8P illustrates an example of injecting a coil 830 without a capsule 115. In this respect, in some embodiments, advantageously, a resonant coil 830 may be implanted just below the skin and serve as a field extender or booster coil since it can resonate with the primary and/or secondary coils 830 of the capsule 115. In this regard, in some embodiments, a coil 830 attached to the capsule is a first coil 830; and the coil 830 illustrated in the example of FIG. 8P is a second coil detached from the capsule. In some embodiments, the second coil 830 comes preloaded into its own separate injector 210 for separate injection.

In addition, power may be conserved by controlling the sensor to intermittently cease detection of the cardiac signal. Additionally or alternatively, the system may detect an AF episode. Upon detection of the AF episode, the system may set a predetermined time period to: (i) monitor and store the processed cardiac signal, and (ii) send the processed cardiac signal to the transmitter for transmission.

In another way of conserving power, in some implementations, the system determines if arrhythmia is suspected. If arrhythmia is suspected, the system increases power intake to the processor, and performs additional analysis on the cardiac signal. If the additional analysis indicates an arrhythmia, the system records the processed signal to random access memory (RAM); and once the RAM reaches a predetermined storage capacity, the system at least one of:

(i) saves the processed signal in RAM to a flash memory, (ii) wirelessly transmits the processed signal to the computing device, or (iii) pauses the recording of the processed signal to RAM in order to wait to be interrogated by the computing device. The determination of if arrhythmia is suspected, may be done using the techniques described in U.S. Pat. No. 9,037,223, or any other technique.

Sensors

In some embodiments the sensors 130 are electrodes. However, any sensing system to sense the cardiac signal may be used. For example, the sensors 130 may include an Electrocardiogram (ECG) sensor; a Photoplethysmography (PPG) sensor; a sensor configured to detect blood pressure or blood flow; an ultrasound sensor; a motion sensor; and/or a sensor configured to detect impedance or admittance.

Further, regarding the interactions between the sensors 130 and the other system components, in some embodiments, the system may, upon detection of the AF episode, set a predetermined time period to: (i) monitor and store the processed cardiac signal, and (ii) send the processed cardiac signal to the transmitter for transmission.

In addition, the sensors 130 may comprise different kinds of sensors (e.g., selected from the kinds of sensors listed above). In some embodiments, the sensors may include first and second sensors that use different wavelengths to detect the cardiac signal from the mammal; in this regard, the processor may be configured to combine the detected cardiac signal from the first sensor with the detected cardiac signal from the second sensor using any of: (i) combination as a ratio of signals, (ii) summation of signals, or (iii) a difference between signals.

Wing(s) or Other Component(s) to Stabilize the Capsule

The wings, which can be folded or unfolded, provide stabilization against rotation of the device, and deploy upon implantation. The example of FIG. 1 shows the wireless charging and communications coils enclosed in the core/lumen of the device; however, alternate designs include having the coil integrated with the wings or provide a large diameter coil for improved power/data transfer.

Any wing configuration may be used. For instance, FIG. 8A illustrates an example of a top view of a capsule 115 where the wings 125 are attached to a first side 805 and a second side 810 of the capsule 115. In some implementations, the wings 125 may expand outwardly from one or both of the sides 805, 810 upon deployment into a mammal. Further, in the example of FIG. 8A, the illustrated wings 125 have a rectangular shape. However, the wings may have any geometric shape. For example, the wings 125 may have rounded corners and/or walls, or the wings 125 may be in an elliptical shape, etc. In some embodiments, the wing(s) are not planar (e.g., the wing(s) have a spiral or tubular shape). In some embodiments, the wing(s) are an integral part of the capsule such that the capsule body itself is shaped as an expandable prolate spheroid with a flat cross section.

Moreover, in the example of FIG. 8A (as well as the examples of FIGS. 8B-D), the wings 125 are in a first state while the capsule 115 is in the injector 210. In the first state (e.g., a state for insertion), the wings are pressed against the capsule 115 so that the capsule and wings fit into the injector 210. Subsequently, when the capsule 115 is deployed into the mammal, the wings 125 enter a second state (e.g., a deployed state) by expanding outwardly from the capsule in a hinge-type motion to anchor the capsule 115 in place. Alternatively, the wings 125 may expand outwardly by uncompressing (e.g., in the first state the wings are compressed, and in the second state the wings are uncompressed). In some implementations, the materials of the wings 125 and capsule 115 are selected such that the wings 125 transition from the first state to the second state upon deployment (e.g., the materials are selected to create a biasing force so that the wings 125 transition from the first state to the second state upon deployment).

In addition, in the examples of FIGS. 8A-8D, the wings 125 may be made of a flexible material and/or a bio-inert material. Furthermore, in some embodiments, the wings 125 are connected to the capsule 115 because the wings 125 and capsule 115 are manufactured together to be part of the same piece. In some embodiments, the wings 125 are attached to the capsule 115 by one or more hinge mechanisms.

In another example, FIG. 8B illustrates a top view of a capsule 115 where the wings 125 (illustrated by the shaded area of FIG. 8B) are attached to a front end 815 and a back end 820 of the capsule 115. In this regard, the wings 125 are in a first state while the capsule 115 is in the injector 210. In the first state (e.g., a state for insertion), the wings are pressed against the capsule 115 so that the capsule and wings fit into the injector 210. Subsequently, when the capsule 115 is deployed into the mammal, the wings 125 enter a second state (e.g., a deployed state) by expanding outwardly from the capsule in a hinge-type motion to anchor the capsule 115 in place. Additionally, in the example of FIG. 8B, the illustrated wings 125 have a rectangular shape. However, the wings may have any geometric shape. For example, the wings 125 may have rounded corners and/or walls, or the wings 125 may be in an elliptical shape, etc.

In another example, FIG. 8C illustrates a front view of a capsule 115 where the wings 125 unroll outwardly from the first side 805 and/or the second side 810 of the capsule 115. In some embodiments, in the first state, the wings 125 encircle an entire circumference of the capsule 115. In other embodiments, in the first state, the wings 125 only partially encircle a circumference of the capsule 115. In some embodiments, the wings are forced outwardly by twisting either the push-rod 230 or the entire injector device 210 to rotate the capsule 115.

Further, although the example of FIG. 8C, as well as the examples of FIGS. 8A and 8D, are illustrated to include two wings, it should be understood that any number of wings may be used. For instance, there may be only one wing (e.g., either on the first side 805 or the second side 810); alternatively, there may be a plurality of wings on one or both of the first side 805 or the second side 810.

In another example, FIG. 8D illustrates a top view of a capsule 115 where the wings 125 expand in an umbrella-type motion from the first side 805 and/or the second side 810 of the capsule 115. Direction of motion arrows 825 illustrate the direction of motion if the wings 125 as the wings expand outwardly from the capsule 115.

In two more examples, FIG. 8E illustrates first external coil embodiment 801, which shows a top view of a capsule 115 where, for stabilization of the capsule, preformed coils 830 are deployed from the first side 805 and/or the second side 810 of the capsule 115. FIG. 8E further illustrates a second external coil embodiment 802, which shows a top view of a capsule 115 where, for stabilization of the capsule, preformed coil 831 is deployed from both the first side 805 and the second side 810 of the capsule 115.

In yet another example, there are no external wing(s) on the capsule 115, and the capsule 115 is stabilized by other means. For instance, in the example of FIG. 8F, the capsule is stabilized by transitioning from rolled state 840 to unrolled state 845.

Moreover, it should be understood that the examples of FIGS. 8A-8F may be combined in any suitable fashion. For instance, there may be a rectangular wing (e.g., from FIG. 8A) on the first side 805, and an umbrella-type wing (e.g., from FIG. 8D) on the second side 810 of the capsule 115.

Injector Device—Example Implementations

Figure 9A:
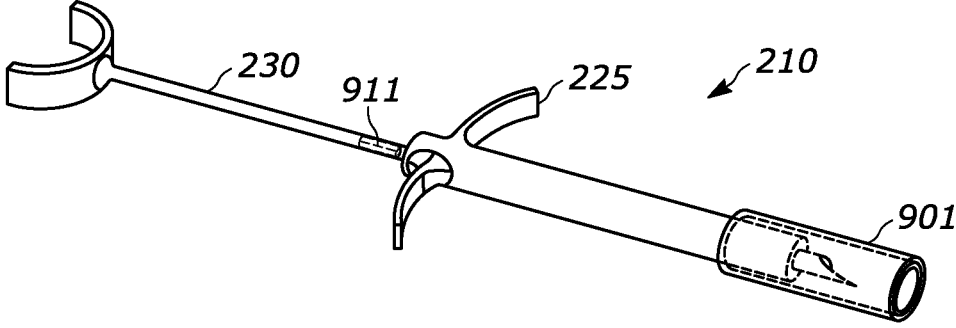
FIG. 9A illustrates an example injector.

The following section will describe various example embodiments of the injector 210. In this regard, in the example of FIG. 9A, some embodiments of the injector 210 include three main components: (1) a beveled needle, (2) an outer casing, and (3) a plunger. Some embodiments also include a cap 901 for protection against the sharp needle tip. Moreover, in some embodiments, the coils 830 trail off the back of the capsule 115. Thus, advantageously, some implementations also include slit 911 on the pushrod 230 to hold the coils 830 as the capsule 115 is injected.

Figure 9B:
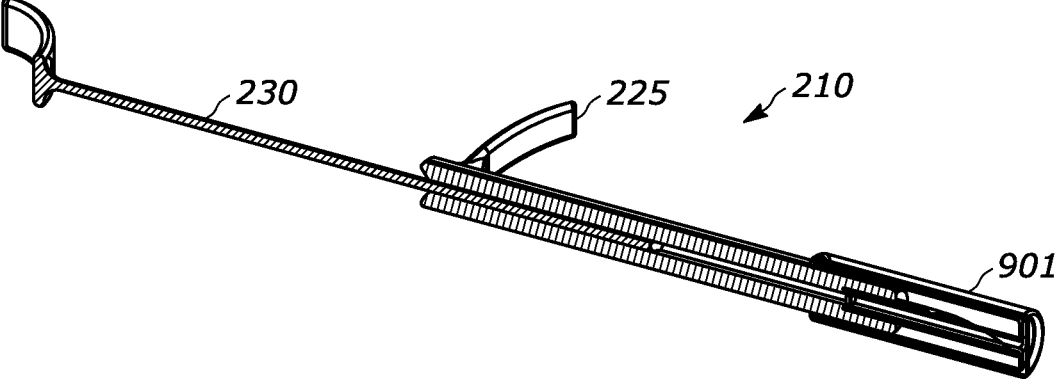
FIG. 9B illustrates a cutaway view of an example injector.

The needle may be placed inside of the outer casing which has handles so the user can comfortably hold the device with one hand. The needle is inserted into only the end portion of the outer casing, as opposed to inserting the needle the entire length of the casing. This way, it is possible to design the core/track of the casing to fit the ovular shape of the capsule in order to prevent rotation and ensure proper orientation upon implantation. The plunger will be placed inside the needle behind the capsule and may extend outside the back of the outer casing. The plunger may utilize the same cross-sectional dimensions as the capsule. The injector may also come with a basic cap that encases the needle point. The cap utilizes an inner rod that extends into the needle cannula and presses against the ECG capsule, preventing unwanted movement of the capsule prior to the implantation procedure (see FIG. 9B).

Beveled Needle

In some embodiments, the tip of the needle utilizes two bevels in order to create a sharp point that is able to puncture the skin and reduce tissue damage during the injection procedure. The secondary bevel angle is created by rotating the needle 45° along its axis and again grinding the point at 17° on both sides (see FIG. 9C, which illustrates a rotated view (45°) of the injector tip showing secondary bevel angle created to reduce the tissue damage during insertion).

Figure 9D:
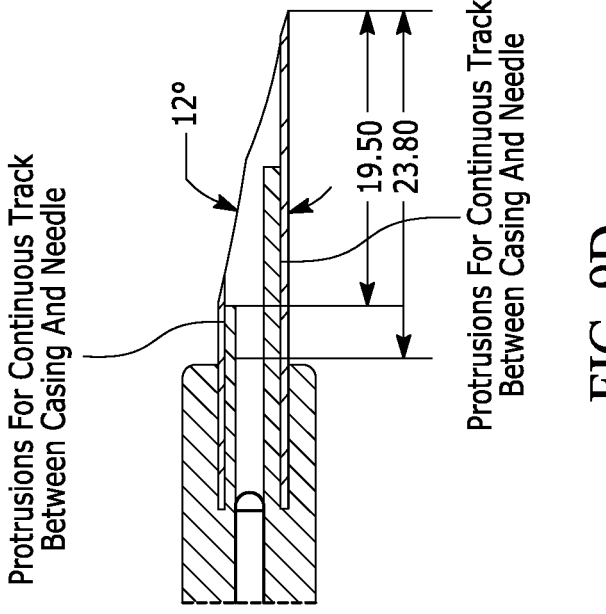
FIG. 9D illustrates an example primary bevel angle, and further illustrates protrusions that enable a continuous track between a casing and needle of an example injector.
Figure 9C:
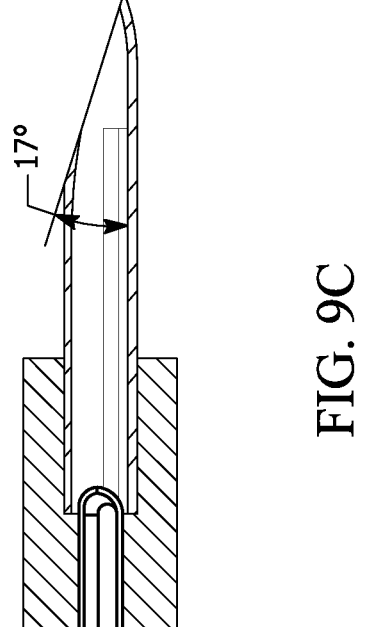
FIG. 9C illustrates a rotated view (45°) of the injector tip showing secondary bevel angle created to reduce the tissue damage during insertion.

The primary bevel angle is created by grinding the needle tip at 12° (see FIG. 9D). These example bevel angle values are consistent with the standards for typical hypodermic needles found in ISO 7864:2016(en). The beveled tip of the needle is approximately 1.95 cm total and extends approximately 2.38 cm beyond the front of the outer casing (see FIG. 9D).

Figure 9E:
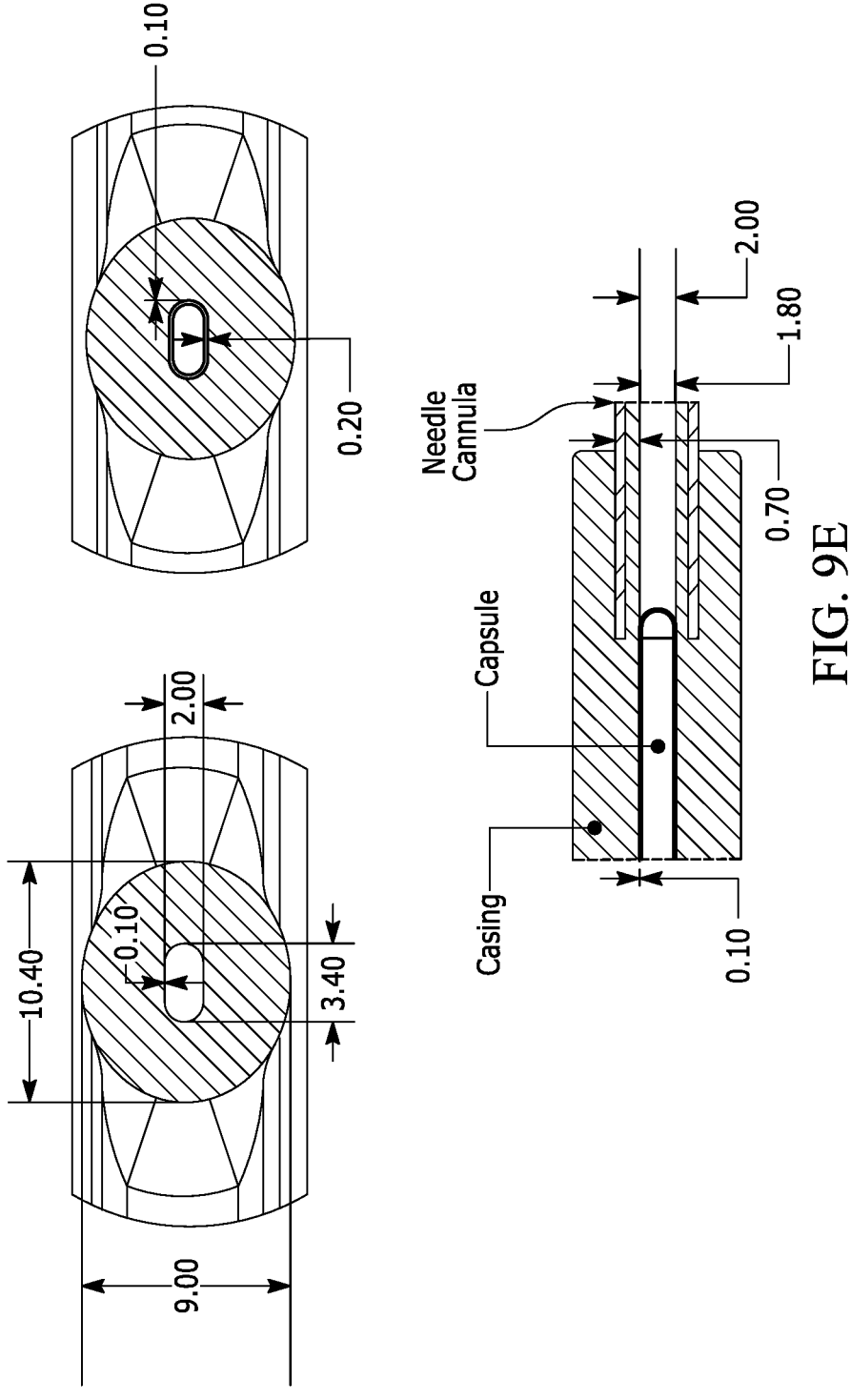
FIG. 9E illustrates example dimensions of an injector.

The needle has an inner diameter of 3.4 mm and an outer diameter of 4.4 mm so that it can sufficiently hold the ECG capsule. The design of the capsule has a width of 3.2 mm and a height of 1.8 mm, thus there is a total of 0.2 mm clearance between the sides of the capsule and the needle wall (0.1 mm clearance between faces). However, because the cannula of the needle is circular and the modified track of the casing is ovular, the height (top to bottom) of the casing track is 2 mm while the height of the needle is 3.4 mm. This results in a drop of 0.8 mm from the bottom of the casing track to the bottom of the needle. This drop could cause the capsule to reorient itself prior to full implantation; to counteract this, some embodiments add two protrusions from the end of the casing that extend into the needle. The basic purpose of these protrusions is to maintain a constant track between the capsule and the needle, which can be visualized as shown in FIG. 9D. This example design allows the capsule to move properly within the casing/needle track when pushed by the plunger during injection according to an engineering sliding fit. To further illustrate, FIG. 9E shows example specific dimensions of the inner geometry of the injector.

Outer Casing

Figure 9F:
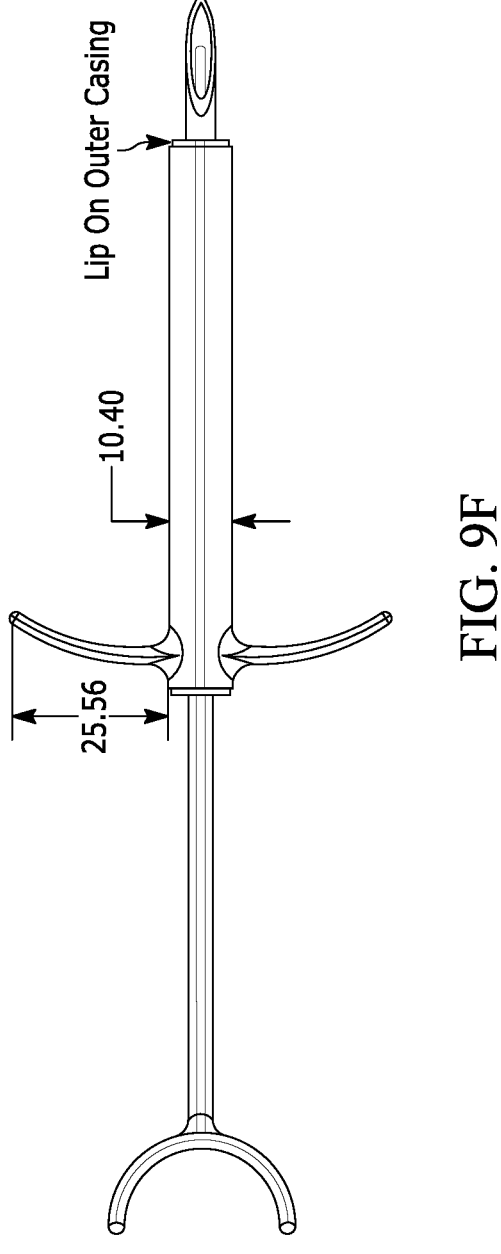
FIG. 9F illustrates an example injector including a lip on the outer casing.

In some embodiments, the outer casing contains the needle, capsule, and plunger. The design of the casing also may be modified to fit the shape of the capsule and plunger. Some implementations have a width of 10.4 mm and height of 9 mm, similar to the size of a pencil, so that it is maneuverable and can easily fit in the clinician's hand. The outer casing provides a lip behind the beveled needle which acts as a visual and physical indicator of insertion depth, as illustrated FIG. 9F. The clinician will not be able to insert the needle beyond the lip of the outer casing to prevent excess tissue damage. This lip is also rounded to reduce unwanted damage to the skin. The outer casing may have handles, similar to those found on syringes, so that the user can easily handle the device. The handles extend out approximately 2.56 cm from the sides of the casing to provide adequate area for placement of the clinician's fingers (see FIG. 9F).

Plunger

In some embodiments, the plunger is a rod that is placed inside the needle, which, when depressed, will push the capsule out of the injector and under the skin during injection. Similar to the capsule and casing, the design of the plunger is modified to fit inside the ovular track of the casing. The height of the plunger may be 1.8 mm and the width will be 3.2 mm. This provides a total clearance of 0.2 mm (0.1 mm clearance between faces) with the track of the casing so that it is able to articulate while still preventing movement in non-axial directions. Some implementations use a second, smaller diameter which provides a method to prevent the removal of the plunger out the back of the casing. However, improved designs include that the plunger is inserted in the casing from the back end; thus, the plunger should have a consistent shape and dimensions along its entire length.

Figure 9G:
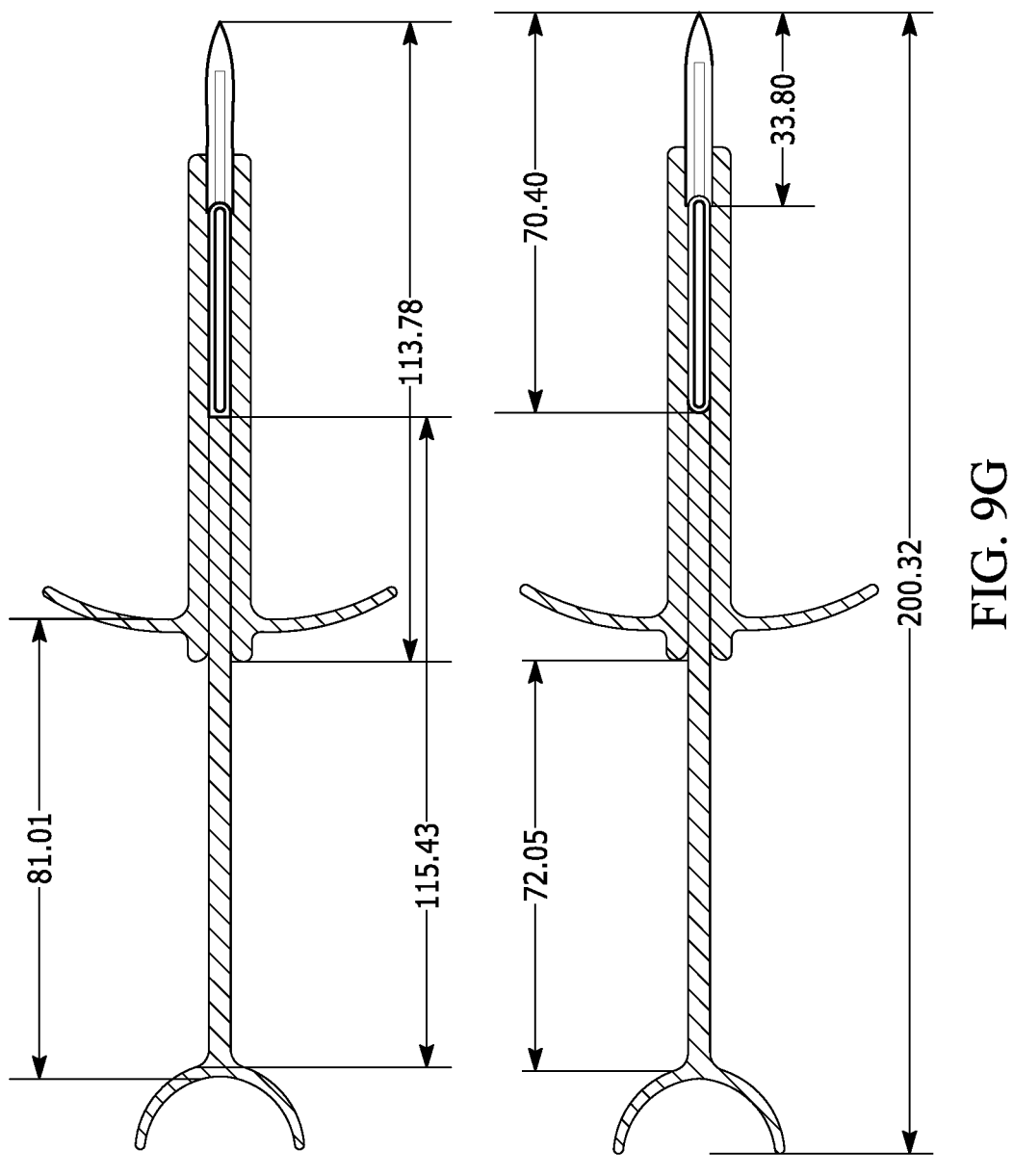
FIG. 9G shows additional examples of injectors.

The plunger should be at least the same length as the injector (casing and needle combined) when fully depressed, so that it is approximately 115 mm long. The length of the casing and needle once assembled is approximately 114 mm, ensuring that fully depressing the plunger will completely eject the capsule from the device. When the capsule is loaded in the device, the plunger extends approximately 72 mm beyond the back of the device. The distance between the base of the plunger thumb rest and base of the casing handles is approximately 81 mm. (See FIG. 9G). This distance was chosen based on the average hand sizes for both men and women and will be discussed further below. Therefore, the user will be able to hold the handles with their index and middle finger and use their thumb to push the plunger down during injection.

Fabrication/Materials

Some embodiments include a 7G needle. In some implementations, the outer casing, along with the handles may be 3D printed using polylactic acid (PLA) and fastened to the stainless steel rod with epoxy. The plunger and thumb rest may also be 3D printed with PLA and assembled with the casing and the needle.

A cap may be placed on the needle for protection, and capsule may be inserted into the outer casing from the back of the injector. The shape of the casing and the shape of the elliptical capsule have to line up for the capsule to be inserted into the injector, which would assist the user in properly aligning the capsule. The cap would also prevent the capsule from going too far forward in the injector. The plunger rod would then be inserted from the back of the injector. The injector may be preloaded with the capsule, and the entire product may be packaged and sterilized together for individual use.

Material Properties

The material of the injector should withstand the force applied to it during injection. In this regard, the typical injection force used by physicians when pressing the plunger is 27.7 N. The cross sectional area of the plunger is 7.07 $mm^2$ (diameter=3 mm), based on one design. Using the force and area, it is possible to calculate the stress, $\sigma$, applied. Some implementations also assume no strain on the plunger, thus $\varepsilon=0.5\%$. It is possible to calculate a Young's modulus, E, with the equation $E=\sigma/\varepsilon$. such that E=784 MPa. PLA has a Young's modulus of 2000 MPa which meets the design requirements of some implementations. PLA also may be shaped using a 3D printer, which is a preferred fabrication method. In some implementations, PLA is selected as the material to be used for the plunger and the handles in the prototyping phase, and an even sturdier material may be used later on manufactured plungers and handles.

Device Size

To determine the appropriate size of the device, the typical hand size of a person was taken into account. Assuming that the length from the thumb to the index finger is approximately ⅔ of the total hand length, and taking the average total hand length of a female as 17 cm (or 7 inches), it was estimated that the length from the thumb to the index finger is about 11 cm. Thus, in some implementations, the injector with a plunger has a length of 8.5 cm so that it easily fits into the hand of an average female for operation. Because it is designed on the smaller end (e.g., using females as a reference), this will allow the device to fit into the hand of any user who operates it.

Operation of Device

Figure 9H:
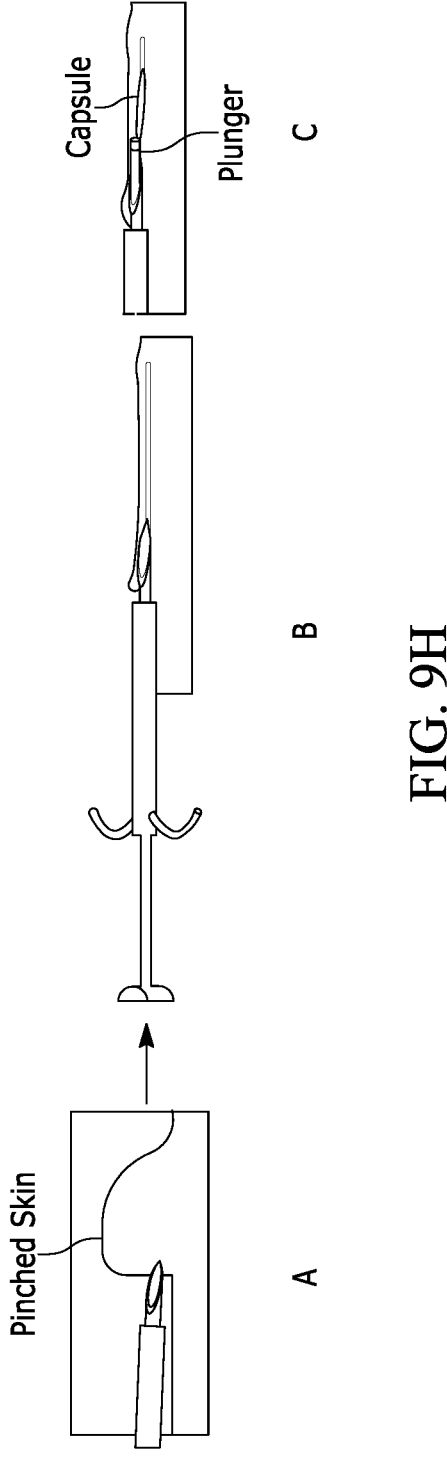
FIG. 9H illustrates three example steps (A, B, C) for inserting an injectable cardiac monitor.

In various examples, there are three main steps involved in the function of the injector: piercing the skin, delivering the capsule in the correct location, and leaving the capsule in the skin when being removed. The 7G needle that is embedded in the outer casing performs the first function of piercing the skin. (see FIG. 9H, step A). Secondly, the device should deliver the capsule in the designated location. As mentioned previously, the capsule may be housed within the needle, preloaded. However, there should be a way to get the capsule from inside the needle, through it, and out the end to ultimately finish within the skin. To accomplish this, some implementations use a plunger to articulate within the needle and push out the capsule. This delivery mechanism is shown in FIG. 9H, step B. Lastly, the device may be removed while leaving behind the capsule in the skin correctly. Because the device simply pushes and leaves the capsule under the skin, it can slide out easily after the capsule is inserted (see FIG. 9H, step C). To summarize, FIG. 9H illustrates steps including: (A) inserting the needle perpendicular to pinched skin; (B) depressing the plunger; and (C) removing device leaving the capsule in place.

The injector is also able to be easily used and manipulated by the user. The user will first pinch a portion of the skin where the capsule will be inserted, and then grip the device with two fingers on the handle and the thumb on the plunger. They will place the device parallel to the chest and perpendicular to the portion of pinched skin and insert the needle up to the outer lip of the casing. They will then depress the plunger all the way in, pushing the capsule down through the needle shaft and under the skin. This mechanism of operation is based on a typical injection procedure by nurses and doctors so will be an understood procedure by the clinician carrying it out. The device will also likely be accompanied by a basic user manual for instructions for use.

Additional Beneficial Features Of Embodiments
Described Herein

The following discusses additional beneficial features, including: (i) snap fit of the cap; (ii) secure retention of the capsule in the device; (iii) minimal skin damage during insertion; (iv) complete injection of capsule; (v) smooth injection of capsule; and (vi) correct orientation of capsule.

For easy cap removal, some embodiments include a cap with a snap fit and an interface with the main body of the device. In addition, a textured surface with ribbing may be included to make it easy to grip and pull off.

To properly contain the capsule inside of the injector, the injector has the capsule inserted into the cannula of the device so it is completely contained. It also has a snug fit inside the cannula so will not fall out prior to pressure being applied to the plunger. In addition, the cap that protects the tip of the needle prevents the capsule from falling out prior to use of the device.

Advantageously, to minimize tissue damage during insertion, in some implementations, the needle point is designed with specific bevel angles to allow for a clean puncture and smooth insertion. In addition, some implementations have a lip on the outer casing of the device, which ensures that the needle is not inserted too far.

To ensure that the capsule is completely injected, the device dimensions should be selected properly. For example, the needle dimensions should be selected such that the needle extends under the skin by a sufficient amount (e.g., 2.4 cm). In addition, the plunger dimensions should be selected such that the plunger extends all the way to the needle tip. The capsule should also be built of a material and shape that is strong enough to push through the tissue and stay in place.

Advantageously, to avoid the capsule becoming stuck during insertion, in some implementations, the injector is designed to be one single smooth channel for the capsule to slide through. The inner casing will be of elliptical shape to conform to the shape of the capsule and will be smaller than the inner diameter of the needle so that the capsule will slide smoothly out of the casing and into the needle portion of the device and then into the skin.

To ensure that the capsule is orientated correctly during insertion, some implementations design the cannula to be of elliptical shape to match that of the capsule. This way, the capsule cannot rotate. In addition, it will have to be inserted in the correct elliptical orientation, as that is the only way that the capsule will fit in the injector.

Force Analysis of Plunger, Capsule, and Injector Handles

The plunger, capsule, and injector handles may be formed of the same materials or different materials. In some examples, the plunger, capsule, and injector are formed of is a Polypropylene (PP) homopolymer, the properties of which are shown below in table 1.

TABLE 1

| Polypropylene (PP) homopolymer material properties | | |
|---|---|---|
| Property | Value | Unit |
| Elastic Modulus | 1790 | MPa |
| Mass Density | 0.034 | lb/in$^3$ |
| Tensile Strength | 33 | MPa |
| Compressive Strength | 39 | MPa |

In some examples, the housing for the capsule is formed of a titanium alloy. The housing may be formed of any suitable biocompatible, corrosion resistant material with a high strength to weight ratio, which titanium is. For example, Ti6Al4V is a common titanium alloy that is used in medical devices, and maybe used for the housing for the ECG capsule. Aged Ti6Al4V alloy, and its material properties are shown below in Table 2.

TABLE 2

| Ti6Al4V alloy material properties | | |
|---|---|---|
| Property | Value | Unit |
| Elastic Modulus | 104800 | MPa |
| Poisson's Ratio | 0.31 | N/A |
| Shear Modulus | 41024 | MPa |
| Mass Density | 0.16 | lb/in$^3$ |
| Tensile Strength | 1050 | MPa |
| Compressive Strength | 970 | MPa |
| Yield Strength | 827 | MPa |
| Thermal Expansion Coefficient | 5e-06 | 1/° F. |

In some embodiments, the handles and/or push-rod comprise a thermoplastic polymer (e.g., acrylonitrile butadiene styrene (ABS) or nylon). In some embodiments, the push-rod and case are made of different materials each with a different stiffness. For example, the push-rod may be made of a material that is more stiff than the case, or vice versa.

In some implementations, the beveled needle is configured to be stored in the case, and then subsequently extend from the case prior to deployment of the capsule. In this regard, in some embodiments, a twisting force on the case extends the beveled needle outside of the case. Alternatively, the beveled needle may be clipped into the case; and a force along an axis of the case may unclip the beveled needle, and extend the beveled needle outside of the case.

In some embodiments, to assist in maintaining orientation of the capsule during deployment, the beveled needle may be oval or square.

Furthermore, a saline rinse or injection may be deployed along with the capsule when the capsule is deployed. For example, a fluid container containing the saline may be connected to the case such that the saline is deployed when the capsule is deployed.

Example Minimalistic Embodiments

Some embodiments include only some of the components described above. For example, in some implementations, the interior of the capsule 115 consists only of an ECG front-end chip 140, and a power transfer/conditioning circuit incorporating a resonant circuit (e.g., a coil and variable capacitor tank circuit). An external device (e.g., a mobile device 165, a patch device 170, and/or a handheld device 175) may provide a tunable oscillating electromagnetic signal that is coupled to the injectable cardiac monitor 110 to deliver power. The external device may adjust its transmit frequency to achieve resonance with the injectable cardiac monitor 110. The output of the ECG front-end 140 is then connected to the variable capacitor of the injectable cardiac monitor's tank circuit. Changes in the ECG signal will result in changes of the injectable device's resonant point, which the transmitting device will track to maintain resonance. The resulting error signal generated at the transmitting device will thus reflect the ECG signal measured by the injectable cardiac monitor 110. A variation on this configuration is to add a microcontroller to the injectable cardiac monitor 110 and employ a digital return channel. In this implementation, there is no need for any power storage capacitors, battery or memory in the injectable cardiac monitor 110, allowing it to be much smaller. Advantageously, this allows the injectable cardiac monitor 110 to have wider lead spacing and more intimate contact between the tissue in order to obtain a much cleaner signal than if a surface ECG was used. Also, the external patch device 170 may be much smaller (e.g., smaller than a quarter).

Additional Aspects

Aspect 1. An injectable cardiac monitor device, comprising:

a sensor configured to detect a cardiac signal from a mammal;

a transmitter configured to transmit the processed signal to a computing device;

and a capsule for injecting into the mammal, the capsule comprising:

a body configured to enclose all of the sensor, and the transmitter; and a wing configured to, upon deployment into the mammal, deploy outwardly from the body of the capsule.

Aspect 2. The device of aspect 1, wherein the wing is comprised in a plurality of flexible wing structures.

Aspect 3. The device of any one of aspects 1-2, wherein the wing is on a front of the capsule.

Aspect 4. The device of any one of aspects 1-3, wherein the wing is on a side of the capsule.

Aspect 5. The device of any one of aspects 1-4, wherein the wing is on a back end of the capsule.

Aspect 6. The device of any one of aspects 1-5, wherein the wing is configured to deploy outwardly from the body of the capsule by expanding from the body of the capsule.

Aspect 7. The device of any one of aspects 1-6, wherein the wing is configured to deploy outwardly from the body of the capsule by unrolling from the body of the capsule.

Aspect 8. The device of any one of aspects 1-7, wherein the wing is configured to deploy outwardly from the body of the capsule by opening, in an umbrella-like motion, from body of the capsule.

Aspect 9. The device of any one of aspects 1-8, wherein the wing is configured to deploy outwardly from the body of the capsule by releasing a preformed coil.

Aspect 10. The device of any one of aspects 1-9, wherein:

the wing is a first wing on a first side of the capsule configured to, upon deployment into the mammal, deploy outwardly from the first side of the body of the capsule; and the device further comprises a second wing on a second side of the capsule, the second wing configured to, upon deployment into the mammal, deploy outwardly from the second side of the body of the capsule.

Aspect 11. The device of any one of aspects 1-10, further comprising:

an energy receiving component configured to power a capacitor stage within the device by inductively harvesting energy from an external charging device;

wherein the capacitor stage is configured to provide power to at least the sensor, and the transmitter.

Aspect 12. The device of aspect 11, wherein the energy receiving component comprises a capacitive membrane, an array of photocells, or an array of ultrasound receivers.

Aspect 13. The device of any one of aspects 1-12, further comprising:

a coil configured to power a capacitor stage within the device by inductively harvesting energy from an external charging device;

wherein the capacitor stage is configured to provide power to the sensor, and the transmitter.

Aspect 14. The device of aspect 13, wherein the coil runs along a longitudinal axis of the body of the capsule.

Aspect 15. The device of aspect 13, wherein the coil comprises:

a primary coil comprised in the first wing and/or the second wing; and a secondary coil comprised in the body of the capsule.

Aspect 16. The device of any one of aspects 1-14, further comprising a capacitor stage configured to:

provide power to the sensor, and the transmitter; and receive power from an external charging device via a coil of the injectable cardiac monitor device.

Aspect 17. The device of aspect 16, wherein the capacitor stage comprises a plurality of electric double-layer capacitors configured in series within the capsule.

Aspect 18. The device of aspect 16, wherein the capacitor stage comprises a plurality of electric double-layer capacitors configured in parallel within the capsule.

Aspect 19. The device of any one of aspects 1-18, wherein the wing is a first wing, and wherein:

the first wing is configured to deploy outwardly from a first side of the body of the capsule by unrolling from the first side of the body of the capsule; and the capsule further comprises a second wing configured to deploy outwardly from a second side of the body of the capsule by unrolling from the second side of the body of the capsule.

Aspect 20. The device of any one of aspects 1-19, wherein the sensor comprises:

an Electrocardiogram (ECG) sensor;

a Photoplethysmography (PPG) sensor;

a sensor configured to detect blood pressure or blood flow;

an ultrasound sensor;

a motion sensor; or a sensor configured to detect impedance or admittance.

Aspect 21. The device of any one of aspects 1-20, wherein the computing device is comprised in a mobile device comprising a smartphone, tablet, or laptop.

Aspect 22. The device of any one of aspects 1-21, wherein the computing device is comprised in a purpose-built bedside monitor.

Aspect 23. The device of any one of aspects 1-22, further comprising a processor configured to process the detected cardiac signal, and wherein the body of the capsule is further configured to enclose the processor.

Aspect 24. The device of aspect 23, wherein:

the sensor is an Electrocardiogram (ECG) sensor; and the processor is configured to:

detect an atrial fibrillation (AF) episode; and upon detection of the AF episode, set a predetermined time period to: (i) monitor and store the processed cardiac signal, and (ii) send the processed cardiac signal to the transmitter for transmission.

Aspect 25. The device of aspect 23, wherein:

the sensor is an Electrocardiogram (ECG) sensor; and the processor is configured to:

determine if arrhythmia is suspected;

if arrhythmia is suspected, increase power intake to the processor, and perform additional analysis on the cardiac signal;

if the additional analysis indicates an arrhythmia, record the processed signal to random access memory (RAM); and once the RAM reaches a predetermined storage capacity, at least one of: (i) save the processed signal in RAM to a flash memory, (ii) wirelessly transmit the processed signal to the computing device, or (iii) pause the recording of the processed signal to RAM in order to wait to be interrogated by the computing device.

Aspect 26. The device of aspect 23, wherein the processor is configured to, via the transmitter, send a ping to the computing device, wherein the ping requests the transmission of power to a capacitor of the injectable cardiac monitor device.

Aspect 27. The device of any one of aspects 1-26, wherein the computing device includes a radio frequency (RF) interface including an antenna configured for wireless transmission.

Aspect 28. The device of any one of aspects 1-27, wherein the computing device includes an electromagnetic or optical interface including an antenna or optical sensors configured for wireless transmission from and to an extracorporeal device.

Aspect 29. The device of any one of aspects 1-28, wherein the processor is configured to conserve power by controlling the sensor to intermittently cease detection of the cardiac signal.

Aspect 30. The device of any one of aspects 1-29, further including an accelerometer, a temperature sensor, and a bioimpedance sensor.

Aspect 31. The device of any one of aspects 1-30, further including:

an optical power receiver configured to optically receive power; and a capacitor stage configured to: (i) be powered by the optical power receiver, and (ii) provide power to the sensor, and the transmitter.

Aspect 32. The device of any one of aspects 1-31, further including:

a power receiver configured to receive power, wherein the power receiver comprises a thermal power receiver, an electromagnetic power receiver, or a vibratory power receiver; and a capacitor stage configured to: (i) be powered by the power receiver, and (ii) provide power to the sensor, and the transmitter.

Aspect 33. The device of any one of aspects 1-32, wherein:

the sensor is a first sensor;

the device further comprises a second sensor configured to use a different wavelength than the first sensor to detect the cardiac signal from the mammal; and the device further comprises a processor configured to combine the detected cardiac signal from the first sensor with the detected cardiac signal from the second sensor using any of: (i) combination as a ratio of signals, (ii) summation of signals, or (iii) a difference between signals.

Aspect 34. The device of any one of aspects 1-33, wherein:

the sensor is an electrocardiogram sensor, and the detected cardiac signal is an electrocardiogram signal; and the device further comprises a processor comprising:

an input stage to receive the electrocardiogram signal, wherein the input stage is a real-time dynamically adjustable signal transformation stage configured to condition the electrocardiogram signal;

an analysis stage coupled to the input stage to receive the conditioned electrocardiogram signal from the input stage, wherein the analysis stage comprises, a transformation stage wherein a frequency, time, or phase domain representation of the conditioned electrocardiogram signal is formed from the conditioned electrocardiogram signal being in a time-domain signal, and an evaluation stage, wherein frequency, time or phase domain features related to the arrhythmias are extracted from the frequency, time, or phase domain representation, wherein the evaluation stage is configured to determine a summed energy over a predetermined range of frequencies, time intervals or phases for the frequency, time, or phase domain representation and configured to normalize the summed energy to the energy at the frequency within the predetermined range of frequencies having the maximum energy to form a spectral frequency dispersion metric (SFDM), spectral time domain dispersion metric (STDM), and/or spectral phase domain dispersion metric (SPDM) over the predetermined range of frequencies, time intervals, or phases; and a classification stage coupled to the evaluation stage to receive the SFDM, STDM, and/or SPDM and to determine whether the mammal is experiencing the arrhythmias.

Aspect 35. The device of any one of aspects 1-34, wherein:

the sensor is an electrocardiogram sensor; and the computing device comprises:

an input stage to receive an electrocardiogram signal as the signal transmitted to the computing device, wherein the input stage is a real-time dynamically adjustable signal transformation stage configured to condition the electrocardiogram signal;

an analysis stage coupled to the input stage to receive the conditioned electrocardiogram signal from the input stage, wherein the analysis stage comprises, a transformation stage wherein a frequency, time, or phase domain representation of the conditioned electrocardiogram signal is formed from the conditioned electrocardiogram signal being in a time-domain signal, and an evaluation stage, wherein frequency, time or phase domain features related to the arrhythmias are extracted from the frequency, time, or phase domain representation, wherein the evaluation stage is configured to determine a summed energy over a predetermined range of frequencies, time intervals or phases for the frequency, time, or phase domain representation and configured to normalize the summed energy to the energy at the frequency within the predetermined range of frequencies having the maximum energy to form a spectral frequency dispersion metric (SFDM), spectral time domain dispersion metric (STDM), and/or spectral phase domain dispersion metric (SPDM) over the predetermined range of frequencies, time intervals, or phases; and a classification stage coupled to the evaluation stage to receive the SFDM, STDM, and/or SPDM and to determine whether the mammal is experiencing the arrhythmias.

Aspect 36. The device of any one of aspects 1-35, wherein the computing device is configured to detect an arrhythmia comprising any of atrial fibrillation, ventricular fibrillation, or atrial flutter.

Aspect 37. The device of any one of aspects 1-36, wherein the computing device is configured to provide and audio or visual warning upon detection of an arrhythmia.

Aspect 38. The device of any one of aspects 1-37, wherein the device further comprises a processor configured to process the detected cardiac signal by any of: filtering, amplifying, and/or digitizing the detected cardiac signal.

Aspect 39. The device of any one of aspects 1-38, further including a mat that is more permeable to magnetic fields than air, water, or tissue.

Aspect 40. The device of any one of aspects 1-39, further comprising:

a first coil configured to power a capacitor stage within the device by inductively harvesting energy from an external charging device; and a second coil detached from the capsule, and configured to resonate with the first coil;

wherein the capacitor stage is configured to provide power to the sensor, and the transmitter.

Aspect 41. An injectable cardiac monitor device, comprising:

a sensor configured to detect a cardiac signal from a mammal;

a processor configured to process the detected cardiac signal;

a transmitter configured to transmit the processed signal to a computing device; and a capsule configured to:

enclose all of the sensor, the processor, and the transmitter;

prior to injection into the mammal, be in a rolled state so as to fit into an injector; and upon injection into the mammal, unroll into an unrolled state.

Other Matters

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of geographic locations.

What is claimed:

1. An injectable cardiac monitor device, comprising:

a sensor configured to detect a cardiac signal from a mammal;

a transmitter configured to transmit the cardiac signal to a computing device; and a capsule for injecting into the mammal, the capsule comprising:

a body configured to enclose all of the sensor and the transmitter;

a wing configured to, upon deployment into the mammal, deploy outwardly from the body of the capsule; and a coil configured to power a capacitor stage within the device by inductively harvesting energy from an external charging device, wherein the capacitor stage is configured to provide power to the sensor and to the transmitter, and wherein the coil is included in the wing.

2. The device of claim 1, wherein the wing is configured to deploy outwardly from the body of the capsule by releasing a preformed coil.

3. The device of claim 1, wherein:

the wing is a first wing on a first side of the capsule configured to, upon deployment into the mammal, deploy outwardly from the first side of the body of the capsule; and the device further comprises a second wing on a second side of the capsule, the second wing configured to, upon deployment into the mammal, deploy outwardly from the second side of the body of the capsule.

4. The device of claim 1, wherein the sensor comprises:

an Electrocardiogram (ECG) sensor;

a Photoplethysmography (PPG) sensor;

a sensor configured to detect blood pressure or blood flow;

an ultrasound sensor;

a temperature sensor;

a motion sensor; or a sensor configured to detect impedance or admittance.

5. The device of claim 1, further comprising a processor configured to process the detected cardiac signal, and wherein the body of the capsule is further configured to enclose the processor.

6. The device of claim 5, wherein:

the sensor is an Electrocardiogram (ECG) sensor; and the processor is configured to:

detect an atrial fibrillation (AF) episode; and upon detection of the AF episode, set a predetermined time period to: (i) monitor and store the processed cardiac signal, and (ii) send the processed cardiac signal to the transmitter for transmission.

7. The device of claim 5, wherein the processor is configured to, via the transmitter, send a ping to the computing device, wherein the ping requests the transmission of power to a capacitor of the injectable cardiac monitor device.

8. The device of claim 1, further including:

an optical power receiver configured to optically receive power; and wherein the capacitor stage is configured to be powered by the optical power receiver.

9. The device of claim 1, further including:

a power receiver configured to receive power, wherein the power receiver comprises a thermal power receiver, an electromagnetic power receiver, or a vibratory power receiver; and wherein the capacitor stage is configured to: (i) be powered by the power receiver.

10. The device of claim 1, wherein:

the sensor is a first sensor;

the device further comprises a second sensor configured to use a different wavelength than the first sensor to detect the cardiac signal from the mammal; and the device further comprises a processor configured to combine the detected cardiac signal from the first sensor with the detected cardiac signal from the second sensor using any of: (i) combination as a ratio of signals, (ii) summation of signals, or (iii) a difference between signals.

11. An injectable cardiac monitor device, comprising:

a sensor configured to detect a cardiac signal from a mammal;

a transmitter configured to transmit the cardiac signal to a computing device; and a capsule for injecting into the mammal, the capsule comprising:

a body configured to enclose all of the sensor and the transmitter;

a wing configured to, upon deployment into the mammal, deploy outwardly from the body of the capsule; and a processor configured to process the detected cardiac signal, and wherein the body of the capsule is further configured to enclose the processor;

wherein:

the sensor is an Electrocardiogram (ECG) sensor; and the processor is configured to:

determine if arrhythmia is suspected;

if arrhythmia is suspected, increase power intake to the processor, and perform additional analysis on the cardiac signal;

if the additional analysis indicates an arrhythmia, record the processed signal to random access memory (RAM); and once the RAM reaches a predetermined storage capacity, at least one of: (i) save the processed signal in RAM to a flash memory, (ii) wirelessly transmit the processed signal to the computing device, or (iii) pause the recording of the processed signal to RAM in order to wait to be interrogated by the computing device.

12. The device of claim 11, further comprising:

an energy receiving component configured to power a capacitor stage within the device by inductively harvesting energy from an external charging device;

wherein the capacitor stage is configured to provide power to at least the sensor and the transmitter.

13. The device of claim 12, wherein the energy receiving component comprises a capacitive membrane, an array of photocells, or an array of ultrasound receivers.

14. The device of claim 11, further comprising:

a coil configured to power a capacitor stage within the device by inductively harvesting energy from an external charging device;

wherein the capacitor stage is configured to provide power to the sensor and the transmitter.

15. The device of claim 14, wherein the coil comprises:

a primary coil comprised in the wing; and a secondary coil comprised in the body of the capsule.

16. The device of claim 11, further comprising a capacitor stage configured to:

provide power to the sensor and the transmitter; and receive power from an external charging device via a coil of the injectable cardiac monitor device.

17. The device of claim 11, further comprising:

a first coil configured to power a capacitor stage within the device by inductively harvesting energy from an external charging device; and a second coil detached from the capsule, and configured to resonate with the first coil;

wherein the capacitor stage is configured to provide power to the sensor and the transmitter.

18. An injectable cardiac monitor device, comprising:

a sensor configured to detect a cardiac signal from a mammal;

a transmitter configured to transmit the cardiac signal to a computing device; and a capsule for injecting into the mammal, the capsule comprising:

a body configured to enclose all of the sensor and the transmitter; and a wing configured to, upon deployment into the mammal, deploy outwardly from the body of the capsule;

wherein:

the sensor is an electrocardiogram sensor, and the detected cardiac signal is an electrocardiogram signal; and the device further comprises a processor comprising:

an input stage to receive the electrocardiogram signal, wherein the input stage is a real-time dynamically adjustable signal transformation stage configured to condition the electrocardiogram signal;

an analysis stage coupled to the input stage to receive the conditioned electrocardiogram signal from the input stage, wherein the analysis stage comprises, a transformation stage wherein a frequency, time, or phase domain representation of the conditioned electrocardiogram signal is formed from the conditioned electrocardiogram signal being in a time-domain signal, and an evaluation stage, wherein frequency, time or phase domain features related to arrhythmias are extracted from the frequency, time, or phase domain representation, wherein the evaluation stage is configured to determine a summed energy over a predetermined range of frequencies, time intervals or phases for the frequency, time, or phase domain representation and configured to normalize the summed energy to the energy at the frequency within the predetermined range of frequencies having the maximum energy to form a spectral frequency dispersion metric (SFDM), spectral time domain dispersion metric (STDM), and/or spectral phase domain dispersion metric (SPDM) over the predetermined range of frequencies, time intervals, or phases; and a classification stage coupled to the evaluation stage to receive the SFDM, STDM, and/or SPDM and to determine whether the mammal is experiencing the arrhythmias.

19. An injectable cardiac monitor device, comprising:

a sensor configured to detect a cardiac signal from a mammal;

a transmitter configured to transmit the cardiac signal to a computing device; and a capsule for injecting into the mammal, the capsule comprising:

a body configured to enclose all of the sensor and the transmitter; and a wing configured to, upon deployment into the mammal, deploy outwardly from the body of the capsule;

wherein:

the sensor is an electrocardiogram sensor; and the computing device comprises:

an input stage to receive an electrocardiogram signal as the signal transmitted to the computing device, wherein the input stage is a real-time dynamically adjustable signal transformation stage configured to condition the electrocardiogram signal;

an analysis stage coupled to the input stage to receive the conditioned electrocardiogram signal from the input stage, wherein the analysis stage comprises, a transformation stage wherein a frequency, time, or phase domain representation of the conditioned electrocardiogram signal is formed from the conditioned electrocardiogram signal being in a time-domain signal, and an evaluation stage, wherein frequency, time or phase domain features related to arrhythmias are extracted from the frequency, time, or phase domain representation, wherein the evaluation stage is configured to determine a summed energy over a predetermined range of frequencies, time intervals or phases for the frequency, time, or phase domain representation and configured to normalize the summed energy to the energy at the frequency within the predetermined range of frequencies having the maximum energy to form a spectral frequency dispersion metric (SFDM), spectral time domain dispersion metric (STDM), and/or spectral phase domain dispersion metric (SPDM) over the predetermined range of frequencies, time intervals, or phases; and a classification stage coupled to the evaluation stage to receive the SFDM, STDM, and/or SPDM and to determine whether the mammal is experiencing the arrhythmias.

* * * * *